(12) United States Patent
Falck

(10) Patent No.: US 11,406,120 B2
(45) Date of Patent: Aug. 9, 2022

(54) LOW MOLECULAR WEIGHT ARABINOXYLANS WITH BRANCHED OLIGOSACCHARIDES

(71) Applicant: CARBIOTIX AB, Lund (SE)

(72) Inventor: Peter Falck, Kävlinge (SE)

(73) Assignee: CARBIOTIX AB, Lund (SE)

(*) Notice: Subject to any disclaimer, the term of this patent is extended or adjusted under 35 U.S.C. 154(b) by 354 days.

(21) Appl. No.: 15/759,228

(22) PCT Filed: Sep. 9, 2016

(86) PCT No.: PCT/SE2016/050843
§ 371 (c)(1),
(2) Date: Mar. 12, 2018

(87) PCT Pub. No.: WO2017/044039
PCT Pub. Date: Mar. 16, 2017

(65) Prior Publication Data
US 2018/0235258 A1    Aug. 23, 2018

(30) Foreign Application Priority Data

Sep. 11, 2015  (SE) .................................. 1551165-2
Oct. 29, 2015  (SE) .................................. 1551401-1

(51) Int. Cl.
*A23K 20/163*      (2016.01)
*C07H 3/06*        (2006.01)
(Continued)

(52) U.S. Cl.
CPC ............ *A23K 20/163* (2016.05); *A23K 10/38* (2016.05); *A23K 50/10* (2016.05); *A23L 2/52* (2013.01);
(Continued)

(58) Field of Classification Search
None
See application file for complete search history.

(56) References Cited

U.S. PATENT DOCUMENTS

2001/0020091 A1*  9/2001  Buchanan ............ A23K 20/163
                                                       536/123
2009/0062232 A1   3/2009  Fujikawa et al.
(Continued)

FOREIGN PATENT DOCUMENTS

EP    2467145 A1    6/2012
EP    2769629 A1    8/2014
(Continued)

OTHER PUBLICATIONS

Collins et al. FEMS Microbial Rev., 29 (1), 3-23. (Year: 2005).*
"3²-α-L-Arabinofuranosyl-xylobiose (A³X)", Megazyme.
Swenne et al., "Large-Scale Production and Characterisation of Wheat Bran Arabinoxylooligosaccharides", Journal of the Science of Food and Agriculture, vol. 86, Issue 11, pp. 1722-1731, May 2, 2006.
(Continued)

*Primary Examiner* — Felicia C Turner
(74) *Attorney, Agent, or Firm* — Moser Taboada

(57) ABSTRACT

The present invention relates to a composition comprising Low Molecular Weight-Arabinoxylan (LMW-AX) with branched oligosaccharides, preferably at least one branched oligosaccharides is positioned at or adjacent to a reducing end of the LMW-AX backbone. The present invention also relates to the production and use thereof. The present invention further relates to a composition comprising Low Molecular Weight-Arabinoxylan (LMW-AX) with oligosaccharides, where a fraction of the Araf units have been removed to improve the yield of oligosaccharides.

20 Claims, 10 Drawing Sheets

Figure 1:
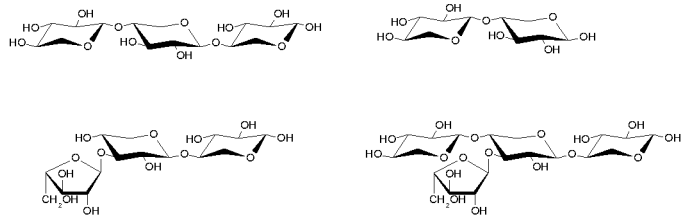
Figure 1:
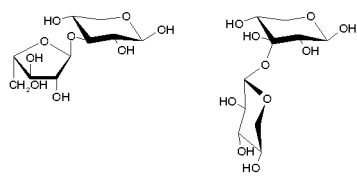
Figure 1:
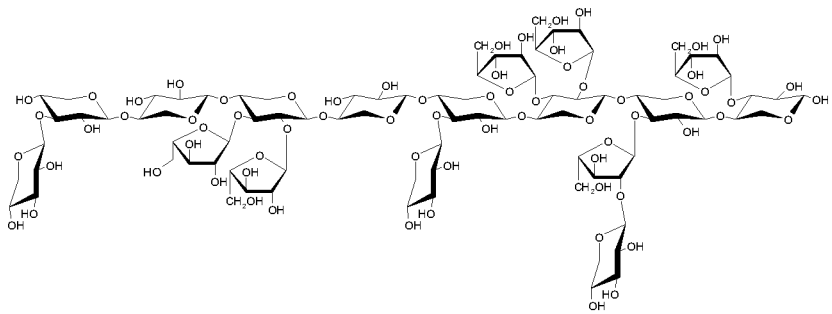
Figure 1:
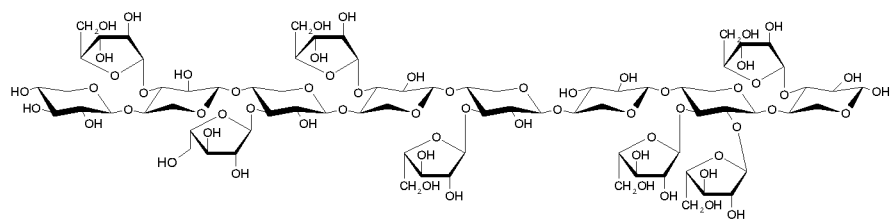

(51) Int. Cl.
| | |
|---|---|
| C12P 19/14 | (2006.01) |
| A23L 33/125 | (2016.01) |
| A23L 33/21 | (2016.01) |
| A23L 7/104 | (2016.01) |
| A23K 10/38 | (2016.01) |
| C08B 37/00 | (2006.01) |
| C12P 19/04 | (2006.01) |
| C12P 19/12 | (2006.01) |
| A23K 50/10 | (2016.01) |
| A61K 31/702 | (2006.01) |
| A23L 2/52 | (2006.01) |
| C12N 9/24 | (2006.01) |

(52) U.S. Cl.
CPC ............. *A23L 7/107* (2016.08); *A23L 33/125* (2016.08); *A23L 33/21* (2016.08); *A61K 31/702* (2013.01); *C07H 3/06* (2013.01); *C08B 37/0057* (2013.01); *C12P 19/04* (2013.01); *C12P 19/12* (2013.01); *C12P 19/14* (2013.01); *C12N 9/24* (2013.01); *Y02E 50/10* (2013.01); *Y02P 60/87* (2015.11)

(56) References Cited

U.S. PATENT DOCUMENTS

| | | | |
|---|---|---|---|
| 2010/0035302 A1 | 2/2010 | Broekaert et al. | |
| 2014/0326421 A1* | 11/2014 | Fallon | D21C 9/005 162/14 |
| 2015/0044356 A1* | 2/2015 | Bootsma | A23K 10/30 426/656 |
| 2015/0225489 A1* | 8/2015 | Broekaert | C08L 5/00 435/99 |

FOREIGN PATENT DOCUMENTS

| | | |
|---|---|---|
| JP | 05253000 A | 10/1993 |
| WO | WO-0047701 A2 | 8/2000 |
| WO | WO-0047701 A3 | 8/2000 |
| WO | WO-2006114095 A1 | 11/2006 |
| WO | WO-2009117790 A2 | 10/2009 |
| WO | WO-2011020853 A1 | 2/2011 |
| WO | WO-2016005519 A1 | 1/2016 |

OTHER PUBLICATIONS

Pastell et al., "Step-Wise Enzymatic Preparation and Structural Characterization of Singly and Doubly Substituted Arabinoxylo-Oligosaccharides with Non-Reducing End Terminal Branches", Carbohydrate Research, vol. 343, Issue 18, pp. 3049-3057, Dec. 8, 2008.

Correia et al., "Structure and Function of an Arabinoxylan-specific Xylanase", The Journal Of Biological Chemistry, vol. 286, Issue 25, pp. 22510-22520, Jun. 24, 2011.

Hooshmand, "Purification and Characterisation of Xylooligosaccharides (XOS) from Wheat-Based Dried Distillers Grains with Soluble", Master Thesis, Department of Chemistry, LUND University, 2012.

Goncalves et al., "Functional Characterization and Synergic Action of Fungal Xylanase and Arabinofuranosidase for Production of Xylooligosaccharides", Bioresource Technology, vol. 119, pp. 293-299, May 2012.

Mandelli et al., "Simultaneous Production of Xylooligosaccharides and Antioxidant Compounds From Sugarcane Bagasse Via Enzymatic Hydrolysis", Industrial Crops and Products, vol. 52, pp. 770-775, Jan. 2014.

McCleary et al., "Hydrolysis of Wheat Flour Arabinoxylan, Acid-Debranched Wheat Flour Arabinoxylan and Arabino-Xylo-oligosaccharides by β-Xylanase, α-L-Arabinofuranosidase and β-Xylosidase", Carbohydrate Research, vol. 407, pp. 79-96, 2015.

International Search Report dated Dec. 12, 2016 for PCT Application No. PCT/SE2016/050843.

Falck "Xy looligosaccharides from Hardwood and Cereal Xylans Produced by a Therostable Xylanase as Carbon Sources for Lactobacillus brevis and Bifidobacterium adolescentis" dx.doi.org/10.1021/jf401249g | J. Agric. Food Chem. 2013, 61, 7333-7340 p. 7333 to 7340.

Falck Peter et al., "Arabinoxylanase from glycoside hydrolase family 5 is a selective enzyme for production of specific arabinoxylooligosaccharides", Food Chemistry, Elsevier Ltd, NL, vol. 242, Sep. 12, 2017 (Sep. 12, 2017), pp. 579-584, XP085213092, ISSN: 0308-8146, DOI: 10.1016/J.FOODCHEM.2017.09048.

Supplementary European Search Report for Application No. EP16844807, dated Apr. 3, 2019.

* cited by examiner

A)

Arabinoxylan-oligosaccharides (XOS+AXOS)

B)

Disaccharides with a (1→3) linkage

C)

Branched oligosaccharides from corn fiber AX obtained by hydrolysis with an arabinoxylan specific endoxylanase

D)

Branched oligosaccharides from wheat bran AX obtained by hydrolysis with an arabinoxylan specific endoxylanase

A)

B)

A)

Arabinoxylan-oligosaccharides (XOS+AXOS)

A)

LOW MOLECULAR WEIGHT ARABINOXYLANS WITH BRANCHED OLIGOSACCHARIDES

FIELD OF THE INVENTION

The present invention relates to low molecular weight arabinoxylans obtained from cereal sources. The low molecular weight arabinoxylans (LMW-AX) are obtained from arabinoxylans by hydrolysis with an arabinoxylan specific endoxylanase. The low molecular weight arabinoxylan contain oligosaccharides branched with at least one arabinose or xylose unit. Low molecular weight arabinoxylans with branched oligosaccharides are particularly useful as feed, food, beverage, personal care ingredients or as nutritional supplements. Further the invention also relates to a process where a fiber isolated from a cereal based ethanol process can be used as a starting substrate. Further the invention also describes how low molecular weight arabinoxylans with branched oligosaccharides produced in connection to an ethanol process can be returned to the process streams to make novel feed products.

Further yet, the invention also relates to how high molecular weight arabinoxylan can be obtained with a high purity. And the present invention also relates to how an insoluble fiber of cellulose and arabinoxylan can be obtained.

Moreover, the present invention relates to how low molecular weight arabinoxylans with oligosaccharides can be obtained from cereal sources. The oligosaccharides are obtained from arabinoxylans by an enzyme cocktail containing arabinofuranosidases and xylanases. The low molecular weight arabinoxylan preparation containing oligosaccharides are particularly useful as feed, food, beverage, personal care ingredients or as nutritional supplements. Further the invention also relates to a process where a fiber isolated from a cereal based ethanol process can be used as a starting substrate. Further the invention also describes how low molecular weight arabinoxylans with oligosaccharides produced in connection to an ethanol process can be returned to the process streams to make novel feed products.

TECHNICAL BACKGROUND

Xylan hemicelluloses are the second most abundant biopolymers in the plant kingdom after cellulose. A common feature for all xylans in higher plants is their backbone of $\beta$-(1→4)-linked D-xylopyranosyl (Xylp) residues. Xylans containing other sugars than xylose are called heteroxylans and can be divided into glucuronoxylans (GX), found in secondary cell walls of dicot plants, or arabinoxylan (AX), found in the primary cell walls of cereals. AX content and composition in cereals varies with botanical source, cultivar and tissue. Most AX is found in the bran tissues (outer- and inner pericarp, testa, nucellar epidermis and associated aleurone layer) majority of which is water-insoluble.

Depending on the source the AX can have different substituents attached as branches on the backbone. The most common structural elements are, I) un-substituted Xylp units (uXyl), II) $\alpha$-(1→2)-linked L-arabinofuranosyl (Araf) linked to a Xylp unit (mXyl2), III) $\alpha$-(1→3)-linked Araf linked to a Xylp unit (mXyl3) and IV) double $\alpha$-(1→2) and $\alpha$-(1→3)-linked Araf linked to a Xylp unit (dXyl). In the case of corn AX the backbone can also be substituted with (1→2) or (1→3)-linked Xylp to the backbone or to Araf substituents. In addition, galactose and glucuronic acid can be present in corn AX. Hydroxycinnamic acid derivatives, mainly ferulic acid (FA), can be ester-linked to position O-5 on a few Araf substituents in native AX.

Two main groups of oligosaccharides can be derived from hydrolysis of AX: xylo-oligosaccharides (XOS) and arabinoxylo-oligosaccharides (AXOS). XOS are xylose linear oligomers, which are linked by $\beta$-(1→4) linkages with the general molecular formula $C_5nH_{8n+2}O_{4n+1}$, where n is the number of xylose units 2-10. XOS are obtained from unbranched regions of AX while AXOS are obtained from branched regions and have a xylose backbone with at least one Araf group attached as a side chain to one of the xylose units. Depending on how many Araf groups are attached, to which residue, and on the chemical linkage type (1→2) and/or (1→3), many different combinations of branched AXOS are possible. Depending on the cereal source other branched oligosaccharides are thinkable. For example in the case of corn AX branched oligosaccharides with (1→3)-linked Xylp to the backbone are possible. AXOS can be distinguished by their degree of substitution (branching) which is usually defined as the ratio between arabinose and xylose units (A/X).

There is a commercial interest of using LMW-AX especially those formulations containing a large portion of oligosaccharides as emerging prebiotics, defined as "a selectively fermented ingredient that results in specific changes in the composition and/or activity of the GI microbiota, thus conferring benefit(s) upon host health". Considerable proofs of AXOS and XOS, prebiotic properties are now available. They are fermented by the faecal microbiota producing health promoting short chain fatty acids acetate, lactate, propionate and butyrate. The prebiotic effect of oligosaccharides obtained from hydrolysed AXs is linked to the molecular weight and the degree of substitution of the backbone (related to the A/X). More complex substitution patterns generally results in slower fermentation and less gas production.

Branched oligosaccharides can potentially be efficient as a more selective and longer lasing prebiotic compared with XOS which ferment rapidly in the proximal colon. AXOS which are branched with arabinose are selective for certain groups of bifidobacteria, considered as one of the most important groups of beneficial bacteria due their ability to stimulate immune system development, produce vitamins, inhibit pathogens, reduce ammonia and cholesterol in the blood and help to restore a healthy gut after antibiotic treatment. The ability among bifidobacteria to utilize branched poly- and oligosaccharides is strain-dependent, meaning that strains can be grouped based on their carbohydrate preference. This means that branched oligosaccharides are first utilized by bifidobacteria or other beneficial bacteria able to remove side branches from the backbone or utilization of smaller branched oligosaccharides. The remaining longer xylose backbone can then be further metabolized in a more distal part of the colon prolonging the prebiotic effect.

Branched oligosaccharides can also find technical applications in food, feed, beverage or personal care applications due to their good water holding capacity compared with unbranched or less branched poly- and oligosaccharides. Especially derived from corn where a considerable amount of proteins are linked to the AX backbone would be suitable as a bulking agent, stabilizer or emulsifier in different applications.

LMW-AX with oligosaccharides have been produced mainly from different cereal brans but also from residues obtained after ethanol fermentation of cereals. Using AX containing residues from an ethanol processes is interesting from an economic standpoint due to the large production volumes annually from cereal sources such as corn and wheat. Dry milling is the most commonly used process for fuel ethanol, comprising the following basic steps: 1) grinding of kernels into flour, 2) slurry in water, 3) heating and liquefaction of starch (with enzymes), 4) fermentation with yeast, 5) distillation of ethanol, 6) separation of wet stillage into thin stillage and wet cake, optionally recovery of corn oil from thin stillage before evaporation into a syrup, 7) mixing of syrup to wet cake, 8) optionally drying of wet distillers grains with solubles into dried distillers grains with solubles (DDGS).

DDGS contains a considerable amount of AX present in the fiber fraction originating from the outer parts of the kernels (bran). The fiber fraction is not considered as a valuable feed component and removing it increases the protein content of the DDGS. The fiber fraction is however, enriched in AX due to the pre-treatment or fermentation step releasing starch and proteins from the fiber. Commercial technologies for wet fractionation of fiber is readily available for dry mill ethanol plants e.g. from Fluid Quip Process Technologies, Springfield Ohio, USA. Wet fractionation performed before fermentation also facilitates increased fermentor capacity 6 to 8%. Another benefit of removing part of the fiber either before or after fermentation is the relative increase in protein content in DDGS for non-ruminant applications.

Utilization of AX for different applications is limited by the availability of suitable starting materials with a low content of starch, proteins and fat. A substrate rich in AX would be more preferable as a starting material to make water-soluble AX since it reduce the need for pre-processing of the fiber by chemical or enzymatic means. Another limitation to the state of the art is the purification of water-soluble AXs since water-soluble proteins, salts and lignins are difficult to remove from the arabinoxylan fraction. This limits the use of arabinoxylans for many applications due to a low purity of the AX extract.

State of the art technology to hydrolyse AXs by commercial endoxylanases, typically belonging to glycoside hydrolase family 10 or 11, is limited to less complex regions of the AX substrate (low A/X ratio) with a sufficient amount of free uXyl. This limits the substrates available to make LMW-AX with oligosaccharides to AX isolated from e.g. testa, nucellar epidermis and parts of the aleurone layer. Technologies that use thermo/chemical methods for producing LMW-AX with oligosaccharides from AX sources have the drawbacks that branches are removed in the process and unwanted side products can be formed such as furfurals and monosaccharides. On the other hand are mechanical treatments to release LMW-AX from AX sources such as dry-ball milling and cavitation not very effective in producing oligosaccharides. Complex AX substrates such as isolated form outer- and inner pericarp (A/X=0.8-1.2 depending on the choice of extraction and source) or densely substituted AX from e.g. corn fiber/bran (A/X=0.5) is therefore not utilized on a commercial scale to make prebiotic preparations consisting of LMW-AX with oligosaccharides.

Insoluble fiber from cellulose is useful as food additives. Cellulose fiber can be made from cereal sources. However, the starting material used by current processes use bran fractions with a large portion of starch, protein and fat. This limits the application of cereal sources for making cellulosic fiber due to expensive pre-processing with enzymes to remove starch and or proteins prior to extraction.

Xylan hemicelluloses are the second most abundant biopolymers in the plant kingdom after cellulose. A common feature for all xylans in higher plants is their backbone of β-(1→4)-linked D-xylopyranosyl (Xylp) residues. Xylans containing other sugars than xylose are called heteroxylans and can be divided into glucuronoxylans (GX), found in secondary cell walls of dicot plants, or arabinoxylan (AX), found in the primary cell walls of cereals. AX content and composition in cereals varies with botanical source, cultivar and tissue. Most AX is found in the bran tissues (outer- and inner pericarp, testa, nucellar epidermis and associated aleurone layer) majority of which is water-insoluble.

Depending on the source the AX can have different substituents attached as branches on the backbone. The most common structural elements are, I) un-substituted Xylp units (uXyl), II) α-(1→2)-linked L-arabinofuranosyl (Araf) linked to a Xylp unit (mXyl2), III) α-(1→3)-linked Araf linked to a Xylp unit (mXyl3) and IV) double α-(1→2) and α-(1→3)-linked Araf linked to a Xylp unit (dXyl). In the case of corn AX the backbone can also be substituted with (1→2) or (1→3)-linked Xylp to the backbone or to Araf substituents. In addition, galactose and glucuronic acid can be present in corn AX. Hydroxycinnamic acid derivatives, mainly ferulic acid (FA), can be ester-linked to position O-5 on a few Araf substituents in native AX.

Two main groups of oligosaccharides can be derived from hydrolysis of AX: xylooligosaccharides (XOS) and arabinoxylooligosaccharides (AXOS). XOS are xylose linear oligomers, which are linked by β-(1→4) linkages with the general molecular formula $C_5nH_8n+2O_4n+1$, where n is the number of xylose units 2-10. XOS are obtained from unbranched regions of AX while AXOS are obtained from branched regions and have a xylose backbone with at least one Araf group attached as a side chain to one of the xylose units. Depending on how many Araf groups are attached, to which residue, and on the chemical linkage type (1→2) and/or (1→3), many different combinations of branched AXOS are possible. Depending on the cereal source other branched oligosaccharides are thinkable. For example in the case of corn AX branched oligosaccharides with (1→3)-linked Xylp to the backbone are possible. AXOS can be distinguished by their degree of substitution (branching) which is usually defined as the ratio between arabinose and xylose units (A/X).

There is a commercial interest of using LMW-AX especially those formulations containing a large portion of oligosaccharides as emerging prebiotics, defined as "a selectively fermented ingredient that results in specific changes in the composition and/or activity of the GI microbiota, thus conferring benefit(s) upon host health". Considerable proofs of AXOS and XOS, prebiotic properties are now available. They are fermented by the faecal microbiota producing health promoting short chain fatty acids acetate, propionate and butyrate. The prebiotic effect of oligosaccharides obtained from hydrolysed AXs is linked to the molecular weight and the degree of substitution of the backbone (related to the A/X). More complex substitution patterns generally results in slower fermentation and less gas production.

AXOS can potentially be efficient as a more selective and longer lasting prebiotics compared with XOS which ferment rapidly in the proximal colon. AXOS which are branched with arabinose are selective for certain groups of bifidobacteria, considered as one of the most important groups of beneficial bacteria due their ability to stimulate immune system development, produce vitamins, inhibit pathogens, reduce ammonia and cholesterol in the blood and help to restore a healthy gut after antibiotic treatment. The ability among bifidobacteria to utilize branched poly- and oligosaccharides is strain-dependent, meaning that strains can be grouped based on their carbohydrate preference. This means that AXOS are first utilized by bifidobacteria or other beneficial bacteria able to remove side branches from the backbone or utilization of smaller branched oligosaccharides. The remaining longer xylose backbone can then be further metabolized in a more distal part of the colon prolonging the prebiotic effect.

Oligosaccharides can also find technical applications in food, feed, beverage or personal care applications due to their good water holding capacity. Especially derived from corn where a considerable amount of proteins are linked to the AX backbone would be suitable as a bulking agent, stabilizer or emulsifier in different applications.

LMW-AX with oligosaccharides have been produced mainly from different cereal brans but also from residues obtained after ethanol fermentation of cereals. Using AX containing residues from an ethanol processes is interesting from an economic standpoint due to the large production volumes annually from cereal sources such as corn and wheat. Dry milling is the most commonly used process for fuel ethanol, comprising the following basic steps: 1) grinding of kernels into flour, 2) slurry in water, 3) heating and liquefaction of starch (with enzymes), 4) fermentation with yeast, 5) distillation of ethanol, 6) separation of wet stillage into thin stillage and wet cake, optionally recovery of corn oil from thin stillage before evaporation into a syrup, 7) mixing of syrup to wet cake, 8) optionally drying of wet distillers grains with solubles into dried distillers grains with solubles (DDGS).

DDGS contains a considerable amount of AX present in the fiber fraction originating from the outer parts of the kernels (bran). The fiber fraction is not considered as a valuable feed component and removing it increases the protein content of the DDGS. The fiber fraction is however, enriched in AX due to the pre-treatment or fermentation step releasing starch and proteins from the fiber. Commercial technologies for wet fractionation of fiber is readily available for dry mill ethanol plants e.g. from Fluid Quip Process Technologies, Springfield Ohio, USA. Wet fractionation performed before fermentation also facilitates increased fermentor capacity 6 to 8%. Another benefit of removing part of the fiber either before or after fermentation is the relative increase in protein content in DDGS for non-ruminant applications.

Xylanases are used for example, in pulp and paper processing, biofuels production, the baking, and the brewing industries and in processing of animal feed. Xylanases are able to hydrolyze the $\beta$-$(1\rightarrow 4)$-xylosidic linkages found in xylan and xylan derived oligosaccharides. Depending on the xylanase used different size of XOS and structures of AXOS can be generated. Family 10 xylanases are known to produce small end products. Family 11 xylanases have the same catalytic mechanism as family 10, but activity is generally higher on polymeric substrates than oligomeric and they have higher activity against insoluble substrates compared with family 10.

State of the art technology to hydrolyse AXs by xylanases, typically belonging to glycoside hydrolase family 10 or 11, is limited to less complex regions of the AX substrate (low A/X ratio) with a sufficient amount of free uXyl. This limits the substrates available to make LMW-AX with oligosaccharides to AX isolated from e.g. testa, nucellar epidermis and parts of the aleurone layer. Technologies that use thermo/chemical methods for producing LMW-AX with oligosaccharides from AX sources have the drawbacks that branches are removed in the process and unwanted side products can be formed such as furfurals and monosaccharides. On the other hand are mechanical treatments to release LMW-AX from AX sources such as dry-ball milling and cavitation not very effective in producing oligosaccharides. Complex AX substrates such as isolated form outer- and inner pericarp (A/X=0.8-1.2 depending on the choice of extraction and source) or densely substituted AX from e.g. corn fiber/bran (A/X=0.5) is therefore not utilized on a commercial scale to make prebiotic preparations consisting of LMW-AX with oligosaccharides.

Utilization of AX for different applications is limited by the availability of suitable starting materials with a low content of starch, proteins and fat. A substrate rich in AX would be more preferable as a starting material to make water-soluble AX since it reduce the need for pre-processing of the fiber by chemical or enzymatic means. Another limitation to the state of the art is the purification of water-soluble AXs since water-soluble proteins, salts and lignins are difficult to remove from the arabinoxylan fraction. This limits the use of arabinoxylans for many applications due to a low purity of the AX extract.

Insoluble fiber from cellulose is useful as food additives. Cellulose fiber can be made from cereal sources. However, the starting material used by current processes use bran fractions with a large portion of starch, protein and fat. This limits the application of cereal sources for making cellulosic fiber due to expensive pre-processing with enzymes to remove starch and or proteins prior to extraction.

SUMMARY OF THE INVENTION

In one aspect the present invention provides a composition comprising Low Molecular Weight-Arabinoxylan (LMW-AX) with branched oligosaccharides, preferably with at least one Arabinose or Xylose positioned at the reducing end of the oligosaccharide backbone.

In one embodiment the branched oligosaccharides comprise Arabinose and Xylose units, preferably with an Arabinose/Xylose ratio of 0.4-1.2, preferably a ratio of 0.4-1.0, preferably a ratio of 0.45-1.0, preferably a ratio of 0.5-0.9.

In one embodiment the composition has an average molecular weight less than 10 kDa, preferably less than 7.5 kDa, preferably less than 5 kDa, preferably less than 4 kDa, preferably less than 3.7 kDa.

In one embodiment the oligosaccharides contain at least one branch consisting of an $(1\rightarrow 3)$ linked arabinofuranosyl unit or $(1\rightarrow 3)$ linked xylopyranosyl unit linked to the backbone.

In one embodiment the composition comprises disaccharides and the disaccharides are linked with a $(1\rightarrow 3)$ linkage between two xylose units or one arabinose and xylose unit.

In one embodiment the substrate is a fiber isolated from at least one of a fiber containing kernel, fiber containing wet process streams or dry Dried Distillers Grains with Solubles (DDGS), preferably from cereals comprising fibers, preferably cereals comprising arabinoxylan.

In one aspect the present invention provides a process for the production of LMW-AX with branched oligosaccharides, using an arabinoxylan specific endoxylanase.

In one embodiment the starting material is a fiber isolated from at least one of a fiber containing kernel, fiber containing wet process streams or dry Dried Distillers Grains with Solubles (DDGS), preferably from cereals comprising fibers, preferably cereals comprising arabinoxylan, preferably a highly or densely substituted arabinoxylan fraction.

In one embodiment the starting material is a fiber with an arabinoxylan content on dry mass basis that is at least 20%, in another embodiment the arabinoxylan content is at least 25%, in another embodiment the arabinoxylan content is at least 30%, in another embodiment the arabinoxylan content is at least 35%, in another embodiment the arabinoxylan content is at least 37%, in another embodiment the arabinoxylan content is at least 40%. The arabinoxylan content may be at most 90%.

In one embodiment the starting material is a fiber that is isolated with a mechanical separation to increase the arabinoxylan content in the fiber fraction.

Examples of such mechanical separation may be selected from the group consisting of centrifugation, filtration, classification by air and flotation, and any combination thereof, In one embodiment the fiber is used for extraction arabinoxylan which has reduced levels of proteins to reduce foaming during alkaline hydrogen peroxide extraction.

In one embodiment the starting material is obtained from a cereal ethanol plant, preferably a dry mill ethanol plant.

In one embodiment wherein the arabinoxylan substrate for the arabinoxylan specific endoxylanase is a water-soluble arabinoxylan, preferably obtained using a pre-treatment of the fiber with alkali, acid, autohydrolysis, steam explosion, milling, cavitation or enzymes.

In one embodiment low substituted AX is precipitated by acidification of an alkali extraction, and preferably is removed.

In one embodiment the water-soluble arabinoxylan is obtained using a pre-treatment comprising at least one of HCl, H2SO4, NaOH, Ca(OH)2, NH4, and alkaline hydrogen peroxide.

In one embodiment the pre-treatment is repeated multiple times. This repeated pre-treatment implies re-using the extraction liquid to increase the concentration of water-soluble arabinoxylan. The extraction liquid is the liquid obtained after removal of solids after pre-treatment. Repeated pre-treatment may be performed by recirculation of the material in the process or multiple process steps in series.

In one embodiment an alkaline or alkaline hydrogen peroxide pre-treatment is repeated multiple times re-using the extraction liquid to increase the concentration of water-soluble arabinoxylan.

In one embodiment pre-treatment is repeated at least two times, preferably more than two times, preferably by using alkaline or alkaline hydrogen peroxide pre-treatment, preferably by re-using the extraction liquid.

In one embodiment any cellulosic solids remaining after the pre-treatment is reintroduced into a stream from a cereal ethanol plant, preferably a dry mill ethanol plant.

In one embodiment the process is for production of feed products.

In one embodiment the process comprises a fiber processing unit including a reaction unit adapted for alkali extraction and neutralization, or autohydrolysis, or acid hydrolysis and neutralization, or cavitation, or steam explosion, or milling; and a separation unit adapted for at least one solid/liquid separation.

In one embodiment the extraction liquid containing water-soluble arabinoxylan is purified with calcium salts. The purpose of purification with calcium salts is to precipitate impurities.

In one embodiment the purity of water-soluble arabinoxylan after calcium salt precipitation is at least 50%, preferably at least 60%, preferably at least 70%, preferably at least 77%, preferably at least 80%, preferably at least 85%, preferably at least 90%, preferably at least 95%, preferably at most 99%.

In one embodiment calcium hydroxide and/or calcium chloride is used to purify water-soluble arabinoxylan by precipitating impurities.

In one aspect the present invention provides use of a composition according to the present invention or an obtained fraction of LMW-AX with branched oligosaccharides from the process according to the present invention, preferably for introduction into a stream of a cereal ethanol plant, preferably a dry mill ethanol plant.

In one embodiment the use is for production of a prebiotic product, preferably food, feed, beverage ingredient or nutritional supplements.

In one aspect the present invention provides a food, feed, beverage ingredient, or nutritional supplement or a personal care product ingredient comprising the LMW-AX with branched oligosaccharides according to the present invention or obtainable by the process according to the present invention.

The current invention describes how LMW-AX with branched oligosaccharides (FIGS. 1 C and D) or (1→3) linked disaccharides (FIG. 1 B) can be produced using an AX specific endoxylanase. These enzymes are unique in their specificity for branched regions of AX since they do not hydrolyse non-branched regions of the molecule. The oligosaccharides generated in this invention contain at least one branch consisting of an (1→3) Araf or Xylp unit linked to the backbone. Disaccharides that are (1→3) xylose-xylose or arabinose-xylose can also be produced.

LMW-AX obtained after enzymatic hydrolysis of with commercial xylanases (from family 10 or 11) or by thermo/chemical treatments contains arabinoxylan-oligosaccharides (A)XOS that is a mixture of both xylo-oligosaccharides (XOS) and arabinoxylo-oligosaccharides (AXOS) as shown in FIG. 1A. It is clear that the state of the art methods of producing LMW-AX with xylanase hydrolysis from low and medium substituted AX (A/X=0.15–0.35) result in mixtures of XOS and AXOS and usually also significant amounts of monosaccharides mainly xylose. Highly branched AX substrates with a high A/X ratio (0.5-1.2) such as from wheat pericarp AX or very dense corn AX (A/X=0.4-0.6) are not easily hydrolysed by commercial xylanases from either family 10 or 11. Xylanase hydrolysis using commercial xylanases of these substrates is severely limited and no or very few oligosaccharides are obtained.

In the present invention an AX specific endoxylanase is used to produce unique LMW-AX with branched oligosaccharides from different cereal sources useful for their selective fermentative or technical properties. Further, the present invention specifically relates to using an AX specific endoxylanases in hydrolysing highly branched AXs such as derived from wheat bran pericap AX or densely substituted AX from corn fiber to make LMW-AX with branched oligosaccharides. Further, the present invention also describes how fibers isolated from process streams by fiber bypass or separation can be used as a substrate to make the intended LMW-AX with branched oligosaccharides in connection with an ethanol process. Further, the present invention also describes how LMW-AX with branched oligosaccharides from the fiber processing can be reintroduced to make novel animal feed products.

Cereal brans can be used as a starting material for making LMW-AX with branched oligosaccharides. However, in order to obtain a suitable substrate without starch and a reduced amount of proteins a pretreatment is usually needed. A better way would be to use a fiber that has already been processed to release starch and proteins. In a dry mill ethanol process the kernel is grinded, liquefied to solubilize starch and then fermented to ethanol by yeast. During this process the AX is left practically unchanged and is therefore enriched in the fiber fraction. This invention preferentially use fiber isolated from an ethanol process instead of coarse bran to make LMW-AX with branched oligosaccharides. This eliminates the need for an extensive pretreatment which will reduce the number of process steps and overall cost of production.

Figure 2:
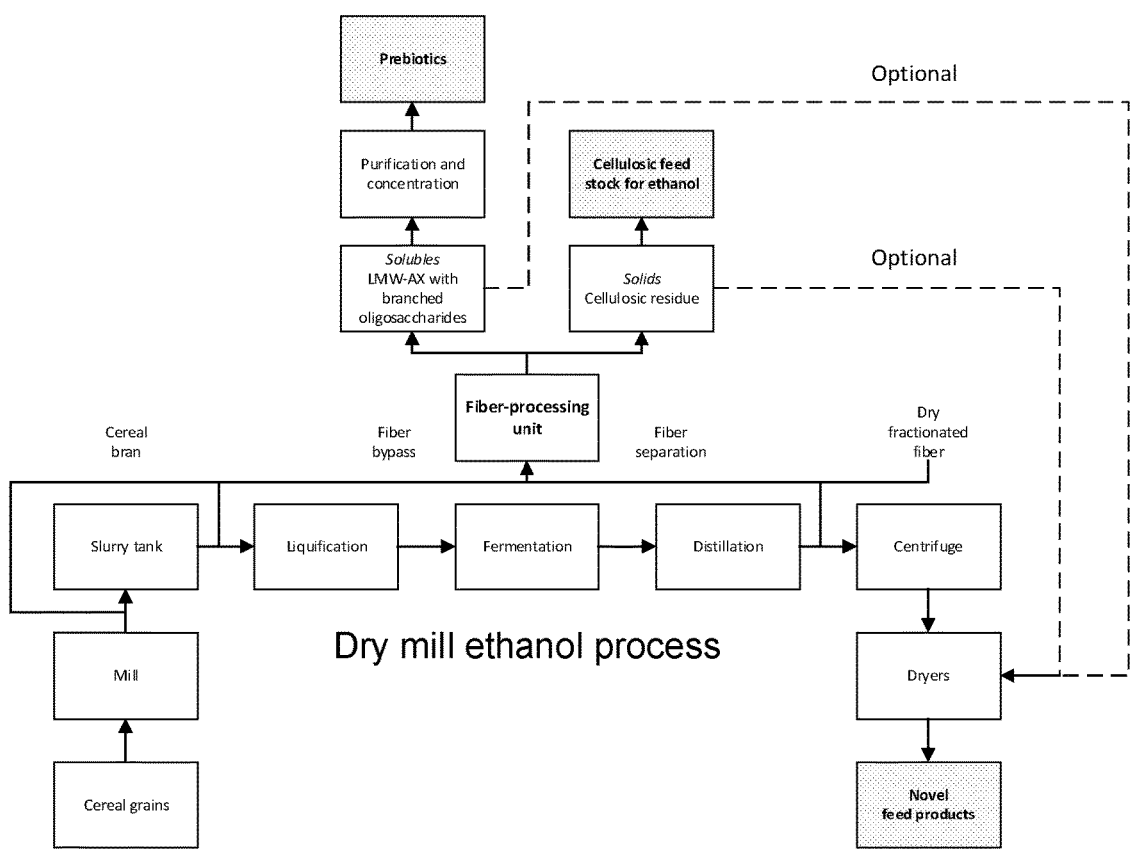

The present invention implies that various starting points in the dry mill ethanol process can be used for isolating a fiber fraction by wet fractionation (FIG. 2). In one embodiment fibers are isolated by wet fractionation before liquefaction, in another embodiment by wet fractionation after the distillation. Various points of fractionation are thinkable and the present invention is not to be seen as limited by the selection of starting point. Production of LMW-AX with branched oligosaccharides is not to be seen as limited only to wet fractionated fiber and various substrates are thinkable as starting materials such as coarse brans. In one embodiment brans isolated from grinded kernels is used as a starting material, in another embodiment fiber dry-fractionated from DDG is used as a starting material.

AX has to be water-soluble for an efficient production of LMW-AX with branched oligosaccharides using an arabinoxylan specific endoxylanase. This can be accomplished by pre-treating the AX containing material by enzymatic, thermo- or chemical treatments. This invention may use alkaline extraction which yields more branched AX compared with steam, acid or enzymatic methods. Preferably using the combination of alkali and hydrogen peroxide to yield a brighter product. Preferably using membrane filtration to recover alkali from the soluble phase containing water-soluble AX after extraction and to remove colored contaminants. Neutralization of the soluble phase containing the isolated water-soluble AX and the cellulosic side product after alkaline extraction can be accomplished using carbon dioxide for an easy neutralization. Optionally treating the isolated soluble fraction with a protease to degrade proteins before dialysis or ultrafiltration. Production of LMW-AX with branched oligosaccharides is not to be seen as limited only to AX isolated by alkaline extraction instead various pre-treatment methods are thinkable such as dry-ball milling, cavitation, autohydrolysis, steam explosion and enzymatic pre-treatments to make the AX fraction water-soluble. Particularly cavitation used in connection with an ethanol process can be used as a pre-treatment method for making water-soluble AX without the need for adding chemicals.

LMW-AX with branched oligosaccharides is obtained by incubating the isolated water-soluble AX with an AX specific endoxylanase exemplified in this invention by an enzyme designated as CtXyl5A. This particular AX specific endoxylanase is from glycoside family 5 (GH5) and originally isolated from *Clostridium thermocellum*. This invention is not to be seen limited by the choice of the arabinoxylan specific endoxylanase with a catalytic module from GH5 or by the natural organism form which the enzyme was isolated. Potentially other bacteria or yeast harbor arabinoxylan specific endoxylanases and the present invention intends to cover all AX specific endoxylanases that specifically hydrolyze substituted regions on an AX molecule to produce branched poly-, oligo- or (1→3) linked disaccharides as end products.

Before the AX specific endoxylanase treatment it is optional to remove a fraction of the branches such as a fraction of the Araf groups, in order to improve the yield of branched oligosaccharides. Removal of substituents can be accomplished by controlled acid hydrolysis or enzymatic hydrolysis using any of the following activities: acetyl xylan esterases, arabinofuranosidase, feruloyl esterases, xylosidase, galactosidase or glucuronidases. Additional purification with desalting, ultrafiltration or decolorizing might be necessary depending on the final application. Preferentially using Nano-filtration to remove water before drying.

In one embodiment the LMW-AX with branched oligosaccharides are produced from the group consisting of cereals. In another more specific embodiment the cereal starting material is selected from the group of cereals such as maize, wheat, sorghum, rice, rye, millets, barley, oat, or but not limited to these. Other possible starting materials are pseudocereals such as, but not limited to, quinoa, amaranth or buckwheat.

LMW-AX with branched oligosaccharides can be added back to process streams (FIG. 2) after fermentation to produce novel feed products with a potentially higher market value compared to traditional DDGS. These novel feed products include prebiotic DDGS for monogastric animals as well as a ruminant DDGS feed for improving rumen development or treating and preventing acidosis. Ruminant DDGS can be created by inclusion of either LMW-AX with branched oligosaccharides alone or in combination with the cellulosic fiber residue. Using carbon dioxide for neutralizing the remaining cellulosic fiber residue also has the added benefit of producing carbonate salts which are normally used in animal feed formulations.

In one embodiment wet fractionated fiber is processed with alkaline hydrogen peroxide to obtain LMW-AX with branched oligosaccharides. The purpose of using hydrogen peroxide in addition to alkali is to brighten the final product.

A. Treating the fibers with alkaline hydrogen peroxide solution and heat;
B. Separation of solids and solubles;
C. Optionally washing the solids with water, from B;
D. Neutralizing of solids from C with carbon dioxide or other acids while using membrane filtration to recover alkali from the soluble phase comprising water-soluble AX, from B;
E. Optionally reintroducing neutralized white cellulosic solids from D into a process stream;
F. Using carbon dioxide or other acids for neutralizing the soluble fraction, from D;
G. Optionally using precipitation or membrane technology to further refine and recover the water-soluble AX, from F;
H. Adding an AX specific endoxylanase and optionally other axillary enzymes for producing LMW-AX with branched oligosaccharides, from F or G;
I. Optionally purify LMW-AX with branched oligosaccharides from H by desalting and activated carbon.
J. Concentration to syrup by nano-filtration optionally followed by drying from H or I.

In all the embodiments the fibers used to produce LMW-AX with branched oligosaccharides can be isolated from a single or a combination of streams or sources. Independent of the starting material the steps for wet fractionation separation consist of:

Taking out the entire or a fraction of a stream containing fibers.

Using a method to separate and isolate fiber particles from the other constituents by centrifugation, filtration or precipitation but not limited to these techniques.

In the embodiments where alkaline or alkaline hydrogen peroxide is used to solubilize AX the residual cellulosic solids after neutralization can give added value to the DDGS stream as an easily digestible fiber for ruminants. It has improved digestive properties due to the fact that the cellulose fiber and remaining AX have been made more accessible for enzymatic degradation by the chemical pre-treatment. In the embodiments where cellulosic solids are returned to the process stream after fiber processing, it is not only limited to DDGS production, instead any stream that ends up as a feed product from the ethanol process is thinkable such as wet distillers grains (WDG) or high protein DDG obtained by wet fractionation. The residual cellulosic solid be also be used as a feedstock for cellulosic ethanol or as a food ingredient. The residual cellulosic solid is especially useful as a food ingredient due to a good water holding capacity. The residual cellulosic solid is also useful for its bulking properties. In one embodiment the product is a food ingredient. In one embodiment the product is a cellulosic fiber. In another embodiment the product is water-soluble AX. In one embodiment the invention may be a cellulosic fiber, water-soluble arabinoxylan, branched Low Molecular Weight-Arabinoxylan or Low Molecular Weight-Arabinoxylan obtained by the process according to the invention.

In the embodiments where LMW-AX with branched oligosaccharides are produced from AX after alkaline or alkaline hydrogen peroxide extractions it is a requirement to use an AX specific endoxylanase, with or without axillary enzymes to produce branched hydrolysis products.

Independent of the starting material and choice of isolation the steps for producing LMW-AX with branched oligosaccharides from AX containing material are:

Optionally grinding the fibers to a smaller particle size
Optionally treating the fibers with amylase and protease
Optionally washing the fibers with water
Various pre-treatments to release AX as water-soluble AX
Optionally separation of solids and solubles before or after an optional neutralization
Optionally reintroducing cellulosic solid residue into process streams for feed
Optionally further refine water-soluble AX by membrane filtration or precipitation
Treating the isolated water-soluble AX with an AX specific endoxylanase
Optionally further purification of the soluble fraction
Optionally introducing obtained LMW-AX with branched oligosaccharides into process streams for feed In all embodiments it is thinkable that the LMW-AX with branched oligosaccharides can be added to any stream that ends up as a feed product from the ethanol process such as wet distillers grains (WDG) or a high protein DDG obtained by wet fractionation and is not only limited to DDGS.

In all embodiments where there is a separation between solids and solubles, it is thinkable that no separation occurs and that the entire processed fiber including both solids and LMW-AX with branched oligosaccharides are returned to any stream that ends up as a feed product in the ethanol process. Or that such preparation are dried and used as a modified fiber together with LMW-AX with branched oligosaccharides in other applications.

In all embodiments where LMW-AX with branched oligosaccharides are produced it is also thinkable that a small fraction of medium molecular weight AX (more than 5 kDa) are still present as a fraction of the total sugars due to an incomplete hydrolysis of the AX substrate.

In one embodiment coarse bran is processed with enzymes, alkaline hydrogen peroxide and an AX specific endoxylanase to obtain LMW-AX with branched oligosaccharides.

A. Treating the bran with amylase and protease followed by washing with water;
B. Treating de-starched and de-proteinized bran from A with alkaline hydrogen peroxide solution and heat;
C. Separation of solids and solubles;
D. Optionally washing the solids with water, from B;
E. Neutralizing of solids from C with carbon dioxide or other acids while using membrane filtration to recover alkali from the soluble phase comprising water-soluble AX, from C;
F. Optionally adding neutralized white cellulosic solids from E into a process stream;
G. Using carbon dioxide or other acids for neutralizing the soluble fraction, from C;
H. Optionally precipitating and removing low branched AX by lowering the pH of the solution, from G;
I. Optionally using precipitation or membrane technology to further refine and recover the water-soluble AX, from H;
J. Adding an AX specific endoxylanase and optionally other axillary enzymes for producing LMW-AX with branched oligosaccharides, from I;
K. Optionally purify LMW-AX with branched oligosaccharides from J by desalting and activated carbon.
L. Concentration to syrup by nanofiltration optionally followed by drying from J or K.

In all embodiments where alkaline hydrogen peroxide is used to make water-soluble AX from cereal residues it is also thinkable that only an alkali is used without adding hydrogen peroxide. This can be the case when the color of the final product does not matter for the final application.

In one embodiment the invention is a process for the production of at least one of a cellulosic fiber, water-soluble arabinoxylan, branched LMW-AX or LMW-AX comprising the steps of:

A. Isolating a fiber fraction from an ethanol process;
B. Increasing the concentration of arabinoxylan in the fiber fraction of step A, by a mechanical process, obtaining a fiber fraction with increased content of arabinoxylan;
C. Treating the fiber fraction with increased arabinoxylan of step B with an alkaline or alkaline hydrogen peroxide solution, obtaining a solution comprising cellulosic solids and water-soluble arabinoxylan;
D. Separating the cellulosic solids of step C from extraction liquid containing water-soluble arabinoxylan followed by neutralizing, washing and drying the cellulosic solids;
E. Optionally repeating extraction of additional fiber fraction re-using the extraction liquid from step D i.e. the previous extraction;
F. Reducing the pH of the extraction liquid obtained after one or multiple extractions with $CO_2$;
G. Treating the extraction liquid obtained after one or multiple extractions with a calcium salt to precipitate impurities and removing impurities;
H. Using precipitation or filtration to recover water-soluble arabinoxylan;
I. Treating the water-soluble arabinoxylan with enzymes to make LMW-AX or branched LMW-AX;
J. Concentrating or drying the LMW-AX products from H and/or I.

Example of enzyme used to treat the water-soluble arabinoxylan may be arabinoxylan specific xylanase and/or xylanase and/or arabinofuranosidase. In one embodiment the enzyme used to treat the water-soluble arabinoxylan may be arabinoxylan specific endoxylanase.

In all the embodiments where calcium salt is added to precipitate impurities it is thinkable that the enzyme added to make branched LMW-AX or LMW-AX are added before the addition of the calcium salt.

Optionally treating the extraction liquid with a weak acid or arabinofuranoseidase to remove a fraction of branching present in the arabinoxylan of the extraction liquid. This treatment with a weak acid may be performed before or after precipitation and/or filtration of the extraction liquid.

In one aspect the present invention provides a composition comprising Low Molecular Weight-Arabinoxylan (LMW-AX) with oligosaccharides, where a fraction of the Araf units have been removed to improve the yield of oligosaccharides.

In one embodiment Low Molecular Weight-Arabinoxylan (LMW-AX) with oligosaccharides comprise Arabinose and Xylose units, preferably with an Arabinose/Xylose ratio of 0.4-1.0, preferably a ratio of 0.4-0.9, preferably a ratio of 0.4-0.8, preferably a ratio of 0.4-0.7, preferably a ratio of 0.4-0.6, preferably a ratio of 0.4-0.5.

In one embodiment the oligosaccharide fraction have an average molecular weight less than 10 kDa, preferably less than 7.5 kDa, preferably less than 5 kDa, preferably less than 2.5 kDa, preferably less than 2 kDa.

In one embodiment the yield of oligosaccharides is improved by combining a xylanase with arabinofuranosidases, preferentially ones able to remove $\alpha$-(1→3)-linked Araf at double substituted Xylp units (dXyl) or able to remove single $\alpha$-(1→2)-linked and $\alpha$-(1→3)-linked Araf at single substituted Xylp units (mXyl). Preferably using a combination of the two different activities of arabinofuranosidases to obtain a high yield of oligosaccharides;

In one embodiment the arabinofuranosidases are selected from the group Arabinoxylan arabinofuranohydrolases (AXHs), preferably selected from the group consisting of arabinoxylan arabinofuranohydrolase-d3 (AXH-d3) or arabinoxylan arabinofuranohydrolase-m2,3 (AXH-m2,3).

In another embodiment the arabinofuranosidase treatment is replaced by a treatment with a weak acid solution before the xylanase treatment, such as, but not limited to, inorganic acids, preferably hydrochloric acid, preferably sulfuric acid, preferably phosphoric acid, preferably nitric acid or preferably acetic acid.

In another embodiment the arabinofuranosidase treatment is replaced by a treatment with steam or hot pressurized water before the xylanase treatment, such as, steam explosion or autohydrolysis.

In one embodiment the xylanase is an endoxylanase, preferably from family 8, 10 or 11, more preferably from family 10 or 11, most preferably from family 10.

In one embodiment the substrate is a fiber isolated from at least one of a fiber containing kernel, fiber containing wet process streams or dry Dried Distillers Grains with Solubles (DDGS), preferably from cereals comprising fibers, preferably cereals comprising arabinoxylan.

In one embodiment the starting material is a fiber isolated from at least one of a fiber containing kernel, fiber containing wet process streams or dry Dried Distillers Grains with Solubles (DDGS), preferably from cereals comprising fibers, preferably cereals comprising arabinoxylan, preferably a highly or densely substituted arabinoxylan fraction.

In one embodiment the starting material is obtained from a cereal ethanol plant, preferably a dry mill ethanol plant.

In one embodiment wherein the arabinoxylan is a water-soluble arabinoxylan, preferably obtained using a pre-treatment of the fiber with alkali, acid, autohydrolysis, steam explosion, milling, cavitation or enzymes.

In one embodiment low substituted AX is precipitated by acidification of an alkali extraction solution, and preferably is removed.

In one embodiment the water-soluble arabinoxylan is obtained using a pre-treatment comprising at least one of HCl, H2SO4, NaOH, Ca(OH)2, NH4, or alkaline hydrogen peroxide.

In one embodiment any cellulosic solids remaining after the pre-treatment is reintroduced into a stream from a cereal ethanol plant, preferably a dry mill ethanol plant.

In one embodiment the process is for production of feed products.

In one embodiment the process comprises a fiber processing unit including a reaction unit adapted for alkali extraction and neutralization, or autohydrolysis, or acid hydrolysis and neutralization, or cavitation, or steam explosion, or milling; and a separation unit adapted for at least one solid/liquid separation.

In one aspect the present invention provides use of a composition according to the present invention or an obtained fraction of LMW-AX with oligosaccharides from the process according to the present invention, preferably for introduction into a stream of a cereal ethanol plant, preferably a dry mill ethanol plant.

In one embodiment the use is for production of a prebiotic product, preferably food, feed, beverage ingredient or nutritional supplements.

In one aspect the present invention provides a food, feed, beverage ingredient, or nutritional supplement or a personal care product ingredient comprising the LMW-AX with oligosaccharides according to the present invention or obtainable by the process according to the present invention.

It is clear that the state of the art methods of producing oligosaccharides with xylanase hydrolysis is most efficient for low and medium substituted AX (A/X=0.15-0.35). Highly branched AX substrates with a high A/X ratio (0.5-1.2) such as from wheat pericarp AX or very dense corn AX (A/X=0.4-0.6) are not easily hydrolysed into oligosaccharides by xylanases alone (FIG. 11).

Figure 11:
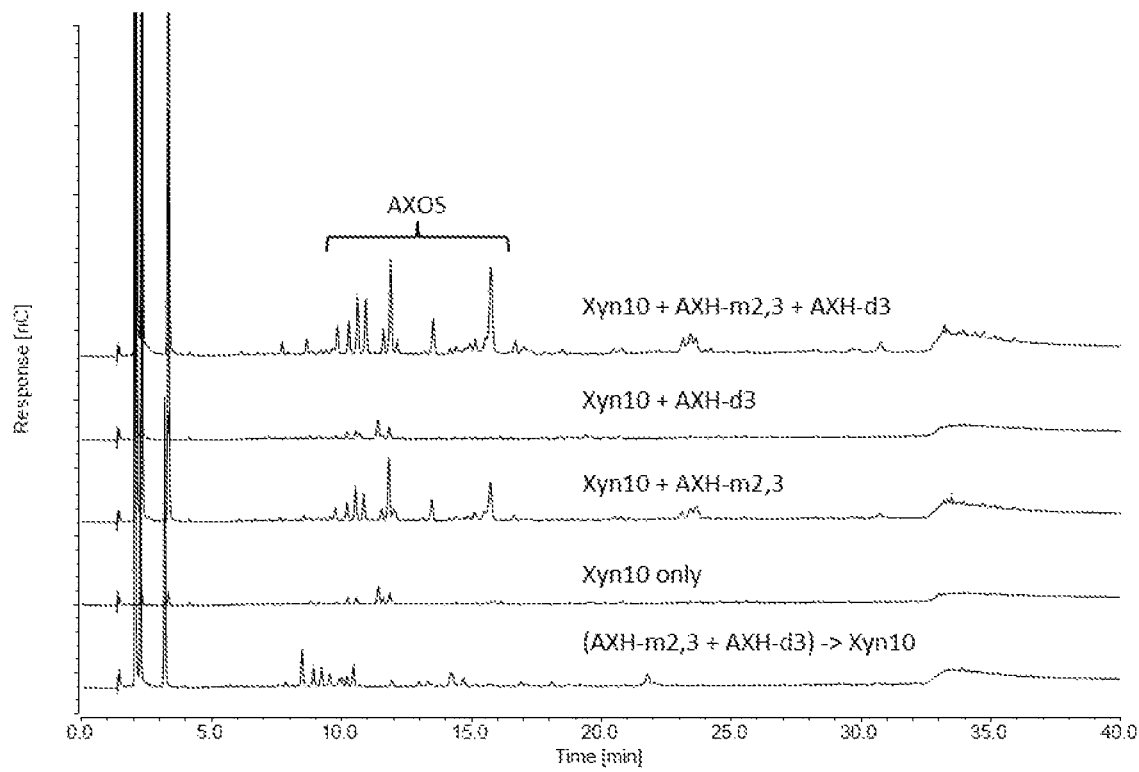

The current invention describes how more oligosaccharides can be produced using a combination arabinofuranosidases and xylanases (FIG. 11). Arabinofuranosidases are specific enzymes unique in removing arabinose groups of the AX backbone opening up the backbone for endoxylanase hydrolysis at specific positions. The combined action facilitates the production of oligosaccharides from complex or densely substituted AX substrates. The oligosaccharides obtained are arabinoxylan-oligosaccharides (A)XOS that is a mixture of both xylo-oligosaccharides (XOS) and arabinoxylo-oligosaccharides (AXOS) as shown in FIG. 1.

Figure 5:
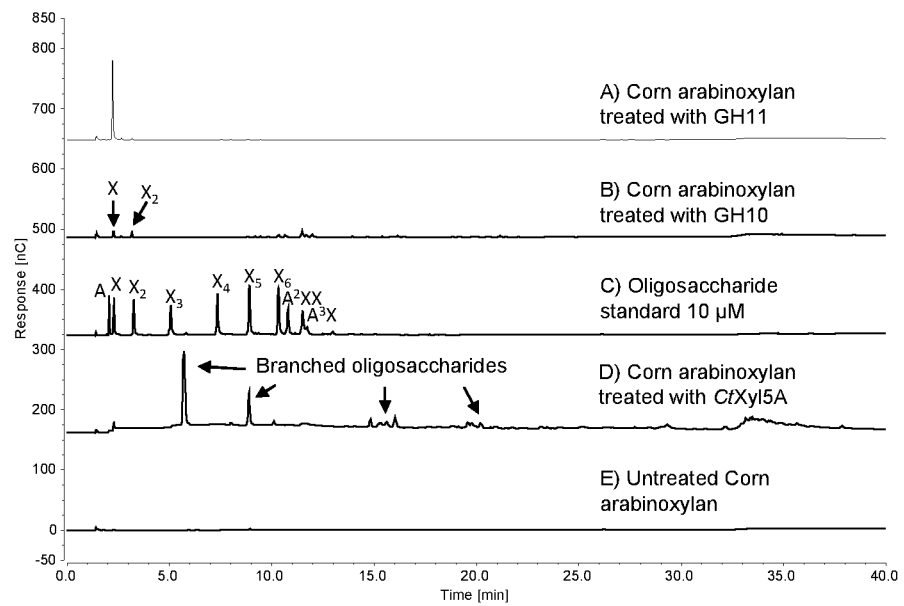
Figure 5:
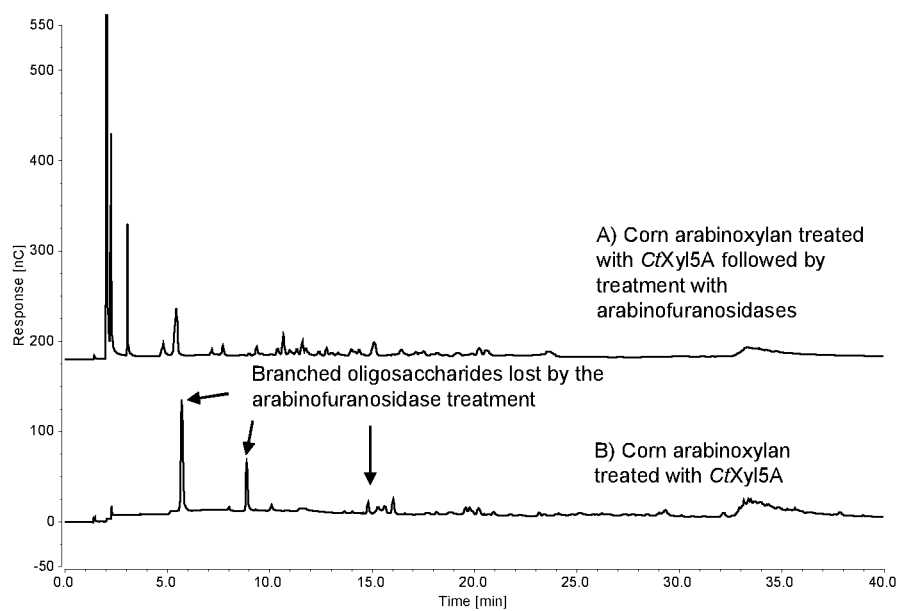

In the present invention a combination of arabinofuranosidases and xylanases is used to produce LMW-AX with oligosaccharides from different cereal sources useful for their selective fermentative or technical properties. Further, the present invention specifically relates to using the enzymes together in cocktails for improved generation of oligosaccharides (FIG. 5). Further, the present invention also describes how fibers isolated from process streams by fiber bypass or separation can be used as a substrate to make the intended LMW-AX with oligosaccharides in connection with an ethanol process. Further, the present invention also describes how LMW-AX with oligosaccharides from the fiber processing can be reintroduced to make novel animal feed products.

Figure 8:
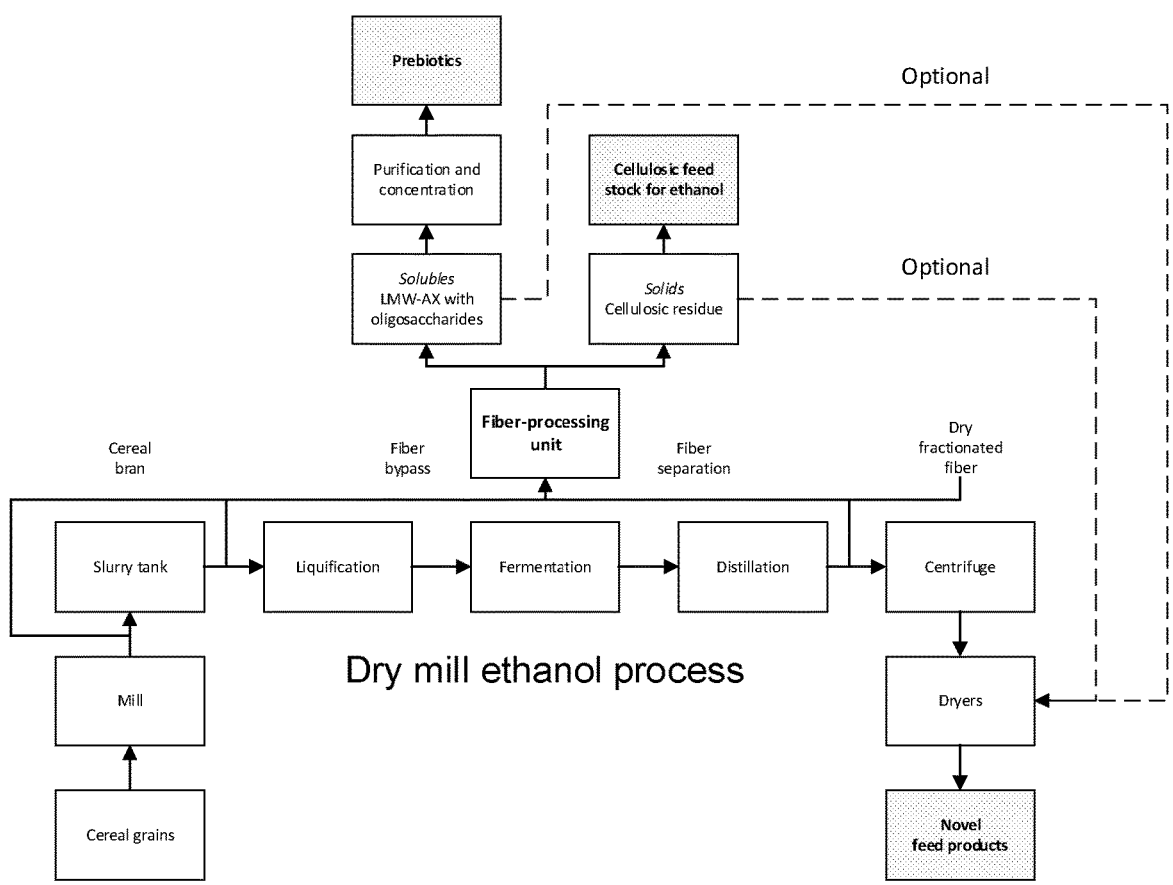

Cereal brans can be used as a starting material for making LMW-AX with oligosaccharides. However, in order to obtain a suitable substrate without starch and a reduced amount of proteins a pretreatment is usually needed. A better way would be to use a fiber that has already been processed to release starch and proteins. In a dry mill ethanol process the kernel is grinded, liquefied to solubilize starch and then fermented to ethanol by yeast. During this process the AX is left practically unchanged and is therefore enriched in the fiber fraction. This invention preferentially use fiber isolated from an ethanol process instead of coarse bran to make LMW-AX with oligosaccharides. This eliminates the need for an extensive pretreatment which will reduce the number of process steps and overall cost of production. The present invention implies that various starting points in the dry mill ethanol process can be used for isolating a fiber fraction by wet fractionation (FIG. 8). In one embodiment fibers are isolated by wet fractionation before liquefaction, in another embodiment by wet fractionation after the distillation. Various points of fractionation are thinkable and the present invention is not to be seen as limited by the selection of starting point. Production of LMW-AX with oligosaccharides is not to be seen as limited only to wet fractionated fiber and various substrates are thinkable as a starting material such as coarse brans. In one embodiment brans isolated from grinded kernels is used as a starting material, in another embodiment fiber dry-fractionated from DDG(S) is used as a starting material.

AX has to be water-soluble for an efficient production of LMW-AX with oligosaccharides from complex AX. This can be accomplished by pre-treating the AX containing material by enzymatic, thermo- or chemical treatments. This invention preferentially uses alkaline extraction which yields more branched AX compared with steam, acid or enzymatic methods. Preferably using the combination of alkali and hydrogen peroxide to yield a brighter product. Preferentially using membrane filtration to recover alkali from the soluble phase containing water-soluble AX after extraction and to remove colored contaminants. Neutralization of the soluble phase containing the isolated water-soluble AX and the cellulosic side product after alkaline extraction can be accomplished using carbon dioxide for an easy neutralization. Optionally treating the isolated soluble fraction with a protease to degrade proteins before dialysis or ultrafiltration. Production of LMW-AX with oligosaccharides is not to be seen as limited only to AX isolated by alkaline extraction instead various pre-treatment methods are thinkable such as dry-ball milling, cavitation, autohydrolysis, steam explosion and enzymatic pre-treatments to make the AX fraction water-soluble. Particularly cavitation used in connection to an ethanol process can be used as a pre-treatment method for making water-soluble AX without the need for adding chemicals.

LMW-AX with oligosaccharides is obtained by incubating the isolated water-soluble AX with arabinofuranosidases that remove a fraction of the branches such as a fraction of the Araf groups, and endoxylanases exemplified in this invention by using two different arabinofuranosidases together with a family 10 endoxylanase. This invention is not to be seen limited by the choice of the arabinofuranosidases and endoxylanase. The present invention intends to cover all combinations of arabinofuranosidases with xylanases to hydrolyze highly substituted or complex regions on an AX molecule to produce oligosaccharides.

Removal of substituents can also be accomplished by controlled acid hydrolysis, steam or autohydrolysis. Other thinkable activities that can be used for improving the generation of oligosaccharides include the following activities: acetyl xylan esterases, feruloyl esterases, xylosidase, galactosidase or glucuronidases. Additional purification with desalting, ultrafiltration or decolorizing might be necessary depending on the final application. Preferentially using Nano-filtration to remove water before drying.

In one embodiment the LMW-AX with oligosaccharides are produced from the group consisting of cereals. In another more specific embodiment the cereal starting material is selected from the group of cereals such as maize, wheat, sorghum, rice, rye, millets, barley, oat, or but not limited to these. Other possible starting materials are pseudocereals such as, but not limited to, quinoa, amaranth or buckwheat.

LMW-AX with oligosaccharides can be added back to process streams (FIG. 8) after fermentation to produce novel feed products with a potentially higher market value compared to traditional DDGS. These novel feed products include prebiotic DDGS for monogastric animals as well as a ruminant DDGS feed for improving rumen development or treating and preventing acidosis. Ruminant DDGS can be created by inclusion of either LMW-AX with oligosaccharides alone or in combination with the cellulosic fiber residue. Using carbon dioxide for neutralizing the remaining cellulosic fiber residue also has the added benefit of producing carbonate salts which are normally used in animal feed formulations.

In one embodiment wet fractionated fiber is processed with alkaline hydrogen peroxide to obtain LMW-AX with oligosaccharides. The purpose of using hydrogen peroxide in addition to alkali is to brighten the final product.

A. Treating the fibers with alkaline hydrogen peroxide solution and heat;
B. Separation of solids and solubles;
C. Optionally washing the solids with water, from B;
D. Neutralizing of solids from C with carbon dioxide or other acids while using membrane filtration to recover alkali from the soluble phase comprising water-soluble AX, from B;
E. Optionally reintroducing neutralized white cellulosic solids from D into a process stream;
F. Using carbon dioxide or other acids for neutralizing the soluble fraction, from D;
G. Optionally using precipitation or membrane technology to further refine and recover the water-soluble AX, from F;
H. Adding arabinofuranosidases and xylanases for producing LMW-AX with oligosaccharides, from F or G;
I. Optionally purify LMW-AX with oligosaccharides from H by desalting and activated carbon.
J. Concentration to syrup by nano-filtration optionally followed by drying from H or I.

In all the embodiments the fibers used to produce LMW-AX with oligosaccharides can be isolated from a single or a combination of streams or sources. Independent of the starting material the steps for wet fractionation separation consist of:

Taking out the entire or a fraction of a stream containing fibers.
Using a method to separate and isolate fiber particles from the other constituents by centrifugation, filtration or precipitation but not limited to these techniques.

In the embodiments where alkaline or alkaline hydrogen peroxide is used to solubilize AX the residual cellulosic solids after neutralization can give added value to the DDGS stream as an easily digestible fiber for ruminants. It has improved digestive properties due to the fact that the cellulose fiber and remaining AX have been made more accessible for enzymatic degradation by the chemical pre-treatment. In the embodiments where cellulosic solids are returned to the process stream after fiber processing, it is not only limited to DDGS production, instead any stream that ends up as a feed product from the ethanol process is thinkable such as wet distillers grains (WDG) or high protein DDG obtained by wet fractionation. The residual cellulosic solid be also be used as a feedstock for cellulosic ethanol or as a food ingredient.

In the embodiments where LMW-AX with oligosaccharides are produced from AX after alkaline or alkaline hydrogen peroxide extractions it is a requirement to use arabinofuranosidases or treatment with steam or acid when it is desired to improve the generation of oligosaccharides.

Independent of the starting material and choice of isolation the steps for producing LMW-AX with oligosaccharides from AX containing material are:
  Optionally grinding the fibers to a smaller particle size
  Optionally treating the fibers with amylase and protease
  Optionally washing the fibers with water
  Various pre-treatments to release AX as water-soluble AX
  Optionally separation of solids and solubles before or after an optional neutralization
  Optionally reintroducing cellulosic solid residue into process streams for feed
  Optionally further refine water-soluble AX by membrane filtration or precipitation
  Treating the isolated water-soluble AX with arabinofuranosidases and xylanases
  Optionally further purification of the soluble fraction
  Optionally introducing obtained LMW-AX with oligosaccharides into process streams for feed In all embodiments it is thinkable that the LMW-AX with oligosaccharides can be added to any stream that ends up as a feed product from the ethanol process such as wet distillers grains (WDG) or a high protein DDG obtained by wet fractionation and is not only limited to DDGS.

In all embodiments where there is a separation between solids and solubles, it is thinkable that no separation occurs and that the entire processed fiber including both solids and LMW-AX with oligosaccharides are returned to any stream that ends up as a feed product in the ethanol process. Or that such preparation are dried and used as a modified fiber together with LMW-AX with oligosaccharides in other applications.

In all embodiments where LMW-AX with oligosaccharides is produced it can be a mixture of longer oligosaccharides (between 10-20 kDa) and smaller oligosaccharides (between 0.4-10 kDa).

In one embodiment coarse bran or pericarp enriched bran (obtained after a xylanase treatment to release low substituted AX or by de-branning) is processed with alkaline hydrogen peroxide to release water-soluble AX followed by hydrolysis using an enzyme cocktail of arabinofuranosidases and xylanases to obtain LMW-AX with oligosaccharides.

A. Optional treating the bran with amylase and protease followed by washing with water;
B. Treating bran, pericarp enriched bran or bran from A with alkaline hydrogen peroxide solution and heat;
C. Separation of solids and solubles;
D. Optionally washing the solids with water, from B;
E. Neutralizing of solids from C with carbon dioxide or other acids while using membrane filtration to recover alkali from the soluble phase comprising water-soluble AX, from C;
F. Optionally adding neutralized white cellulosic solids from E into a process stream;
G. Using carbon dioxide or other acids for neutralizing the soluble fraction, from C;
H. Optionally precipitating and removing low branched AX by lowering the pH of the solution, from G;
I. Optionally using precipitation or membrane technology to further refine and recover the water-soluble AX, from H;
J. Adding arabinofuranosidases and xylanases for producing LMW-AX with oligosaccharides, from I;
K. Optionally purify LMW-AX with oligosaccharides from J by desalting and activated carbon.
L. Concentration to syrup by nanofiltration optionally followed by drying from J or K.

In all embodiments where alkaline hydrogen peroxide is used to make water-soluble AX from cereal residues it is also thinkable that only an alkali is used without adding hydrogen peroxide. This can be the case when the color of the final product does not matter for the final application. In one embodiment the pre-treatment is repeated multiple times. This repeated pre-treatment implies re-using the extraction liquid to increase the concentration of water-soluble arabinoxylan. The extraction liquid is the liquid obtained after removal of solids after pre-treatment. Repeated pre-treatment may be performed by recirculation of the material in the process or multiple process steps in series.

In one embodiment an alkaline or alkaline hydrogen peroxide pre-treatment is repeated multiple times re-using the extraction liquid to increase the concentration of water-soluble arabinoxylan.

In one embodiment pre-treatment is repeated at least two times, preferably more than two times, preferably by using alkaline or alkaline hydrogen peroxide pre-treatment, preferably by re-using the extraction liquid.

In one embodiment the starting material is a fiber with an arabinoxylan content on dry mass basis that is at least 20%, in another embodiment the arabinoxylan content is at least 25%, in another embodiment the arabinoxylan content is at least 30%, in another embodiment the arabinoxylan content is at least 35%, in another embodiment the arabinoxylan content is at least 37%, in another embodiment the arabinoxylan content is at least 40%. The arabinoxylan content may be at most 90%.

In one embodiment the starting material is a fiber that is isolated with a mechanical separation to increase the arabinoxylan content in the fiber fraction.

Examples of such mechanical separation may be selected from the group consisting of centrifugation, filtration, classification by air and flotation, and any combination thereof, In one embodiment the fiber is used for extraction arabinoxylan which has reduced levels of proteins to reduce foaming during alkaline hydrogen peroxide extraction.

In one embodiment the extraction liquid containing water-soluble arabinoxylan is purified with calcium salts. The purpose of purification with calcium salts is to precipitate impurities.

In one embodiment the purity of water-soluble arabinoxylan after calcium salt precipitation is at least 50%, preferably at least 60%, preferably at least 70%, preferably at least 77%, preferably at least 80%, preferably at least 85%, preferably at least 90%, preferably at least 95%, preferably at most 99%.

In one embodiment calcium hydroxide and/or calcium chloride is used to purify water-soluble arabinoxylan by precipitating impurities.

The residual cellulosic solid is especially useful as a food ingredient due to a good water holding capacity. The residual cellulosic solid is also useful for its bulking properties. In one embodiment the product is a food ingredient.

In one embodiment the product is a cellulosic fiber. In another embodiment the product is water-soluble AX. In one embodiment the invention may be a cellulosic fiber, water-soluble arabinoxylan, branched Low Molecular Weight-Arabinoxylan or Low Molecular Weight-Arabinoxylan obtained by the process according to the invention.

In one embodiment the invention is a process for the production of at least one of a cellulosic fiber, water-soluble arabinoxylan, branched LMW-AX or LMW-AX comprising the steps of:

A. Isolating a fiber fraction from an ethanol process;
B. Increasing the concentration of arabinoxylan in the fiber fraction of step A, by a mechanical process, obtaining a fiber fraction with increased content of arabinoxylan;
C. Treating the fiber fraction with increased arabinoxylan of step B with an alkaline or alkaline hydrogen peroxide solution, obtaining a solution comprising cellulosic solids and water-soluble arabinoxylan;
D. Separating the cellulosic solids of step C from extraction liquid containing water-soluble arabinoxylan followed by neutralizing, washing and drying the cellulosic solids;
E. Optionally repeating extraction of additional fiber fraction re-using the extraction liquid from step D i.e. the previous extraction;
F. Reducing the pH of the extraction liquid obtained after one or multiple extractions with CO2;
G. Treating the extraction liquid obtained after one or multiple extractions with a calcium salt to precipitate impurities and removing impurities;
H. Using precipitation or filtration to recover water-soluble arabinoxylan;
I. Treating the water-soluble arabinoxylan with enzymes to make LMW-AX or branched LMW-AX;
J. Concentrating or drying the LMW-AX products from H and/or I.

Example of enzyme used to treat the water-soluble arabinoxylan may be arabinoxylan specific xylanase and/or xylanase and/or arabinofuranosidase.

In all the embodiments where calcium salt is added to precipitate impurities it is thinkable that the enzyme added to make branched LMW-AX or LMW-AX are added before the addition of the calcium salt.

Optionally treating the extraction liquid with a weak acid or arabinofuranosidase to remove a fraction of branching present in the arabinoxylan of the extraction liquid. This treatment with a weak acid may be performed before or after precipitation and/or filtration of the extraction liquid.

SHORT DESCRIPTION OF THE DRAWINGS

FIG. 1. Molecular structures of molecules derived by hydrolysis of arabinoxylans A) Arabinoxylan-oligosaccharides which is a mixture between xylo-oligosaccharides and arabinoxylo-oligosaccharides obtained by commercial xylanases from family 10 or 11, B) disaccharides that are (1→3) linked xylose-xylose or arabinose-xylose generated by an arabinoxylan specific endoxylanase from corn fiber arabinoxylan, C) branched oligosaccharide from corn fiber arabinoxylan generated by an arabinoxylan specific endoxylanase and D) branched oligosaccharide from wheat bran arabinoxylan generated by an arabinoxylan specific endoxylanase.

FIG. 2. Flow chart describing the separation of fibers from kernels, fiber bypass or fiber separation by wet fractionation or from dry fractionated fiber from DDGS. These fibers are then fed to a fiber-processing unit where LMW-AX with branched oligosaccharides is produced as the main product. The cellulosic solid residue after fiber processing is optionally returned to a stream for feed while a fraction of LMW-AX with branched oligosaccharides can be added to introduce prebiotic properties in novel feed product.

Figure 3:
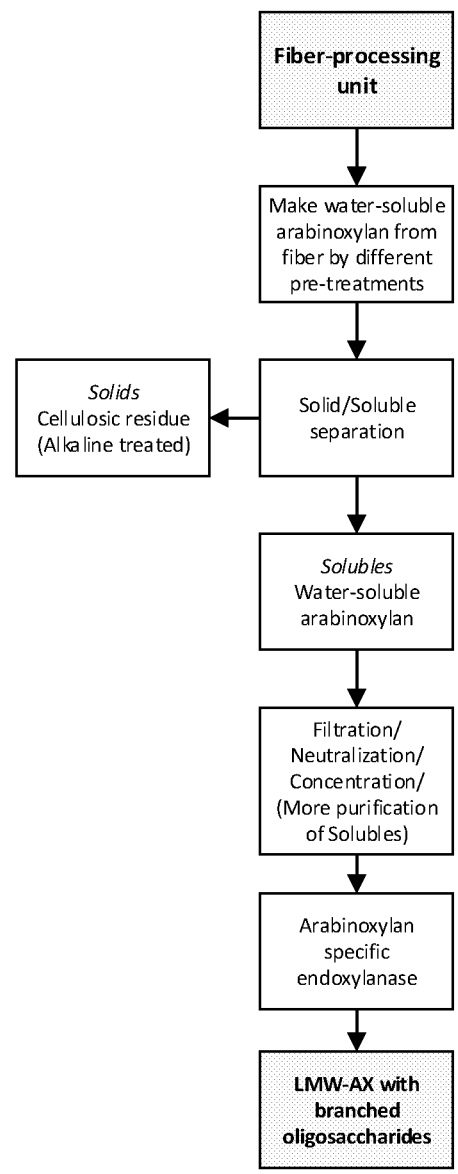

FIG. 3. Flow chart describing the fiber-processing operations in connection to an ethanol process to obtain LMW-AX with branched oligosaccharides.

Figure 4:
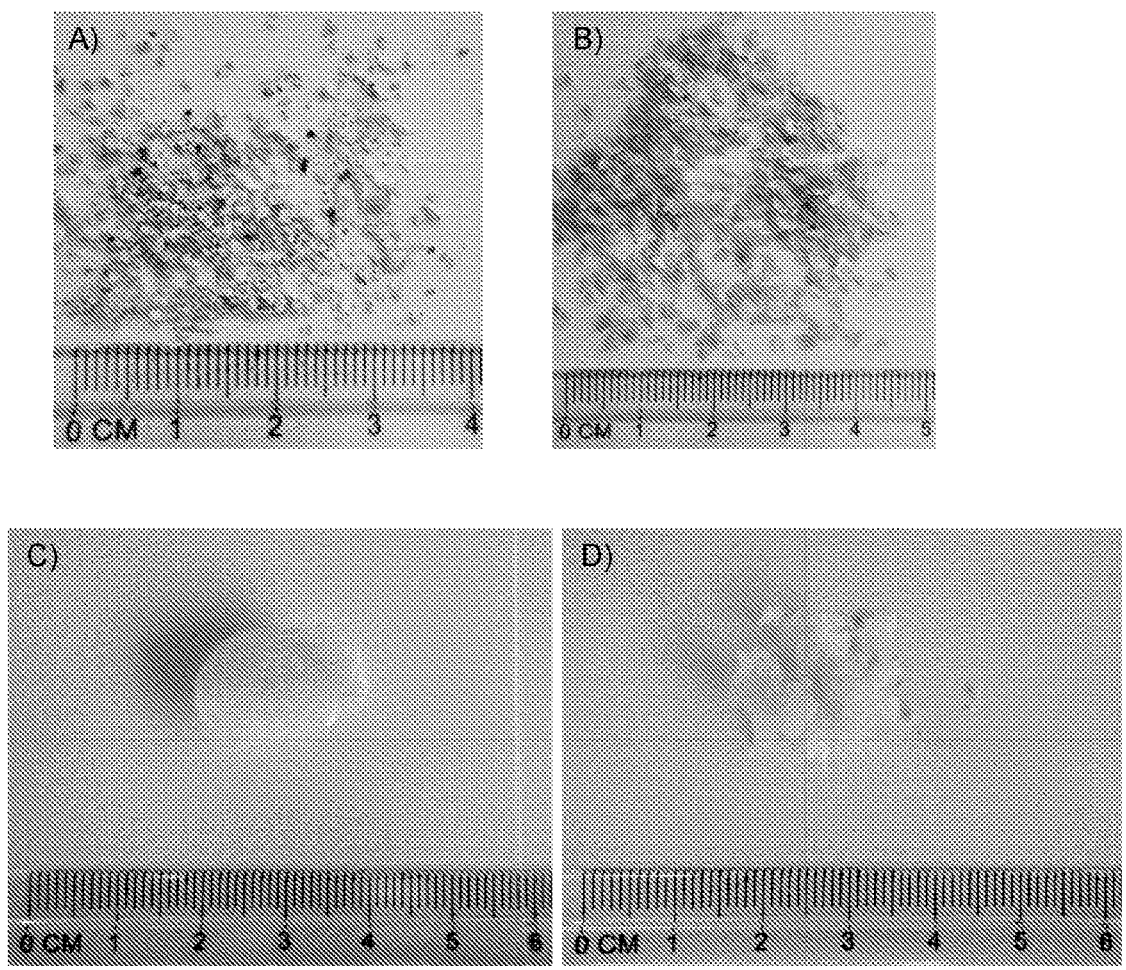

FIG. 4. A) Picture of corn stillage sample, B) picture of fractionated fiber from corn stillage sample, C) freeze dried LMW-AX with branched oligosaccharides from corn AX and D) freeze dried cellulosic residue after alkaline hydrogen peroxide extraction of corn fiber.

FIG. 5. HPAED-PAD chromatogram showing oligosaccharides present in samples A) corn arabinoxylan hydrolyzed with 3 different xylanases and B) branched oligosaccharides obtained from corn arabinoxylan by an arabinoxylan specific endoxylanase CtXyl5A before and after incubation with arabinofuranosidases. Standards are A: arabinose, X: xylose, $X_2$: xylobiose, $X_3$: xylotriose, $X_4$: xylotetraose, $X_5$: xylopentaose, $X_6$: xylohexaose, $A^2XX$: α-(1→2)-arabinofuranosyl-O-(1→4)-xylopyranosyl-β-(1→4)-xylopyranosyl-β-(1→4)-xylopyranosyl, $A^3X$: α-(1→3)-arabinofuranosyl-β-(1→4)-xylopyranosyl-β-(1→4)-xylopyranosyl.

Figure 6:
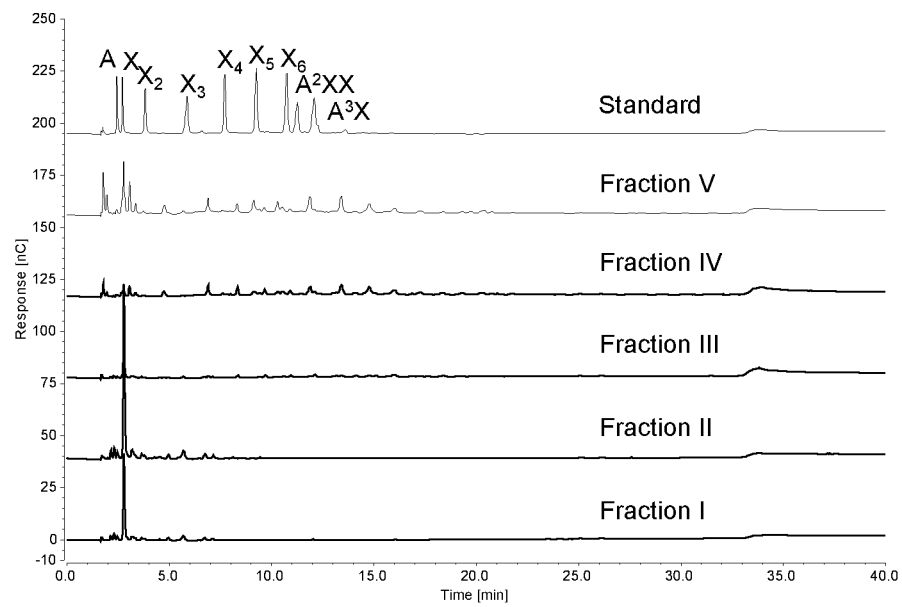

FIG. 6. HPAED-PAD chromatogram showing oligosaccharides present in the different SEC fractions obtained from wheat bran LMW-AX with branched oligosaccharides that was produced by an arabinoxylan specific endoxylanase CtXyl5A. Standards are A: arabinose, X: xylose, $X_2$: xylobiose, $X_3$: xylotriose, $X_4$: xylotetraose, $X_5$: xylopentaose, $X_6$: xylohexaose, $A^2XX$: α-(1→2)-arabinofuranosyl-β-(1→4)-xylopyranosyl-β-(1→4)-xylopyranosyl-β-(1→4)-xylopyranosyl, $A^3X$: α-(1→3)-arabinofuranosyl-β-(1→4)-xylopyranosyl-β-(1→4)-xylopyranosyl.

Figure 7:
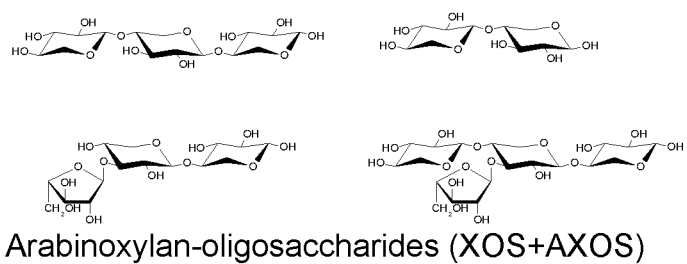

FIG. 7. Arabinoxylan-oligosaccharides derived by hydrolysis of arabinoxylans which is a mixture between xylo-oligosaccharides and arabinoxylo-oligosaccharides.

FIG. 8. Flow chart describing the separation of fibers from kernels, fiber bypass or fiber separation by wet fractionation or from dry fractionated fiber from DDGS. These fibers are then fed to a fiber-processing unit where LMW-AX with oligosaccharides is produced as the main product. The cellulosic solid residue after fiber processing is optionally returned to a stream for feed while a fraction of LMW-AX with oligosaccharides can be added to introduce prebiotic properties in novel feed product.

Figure 9:
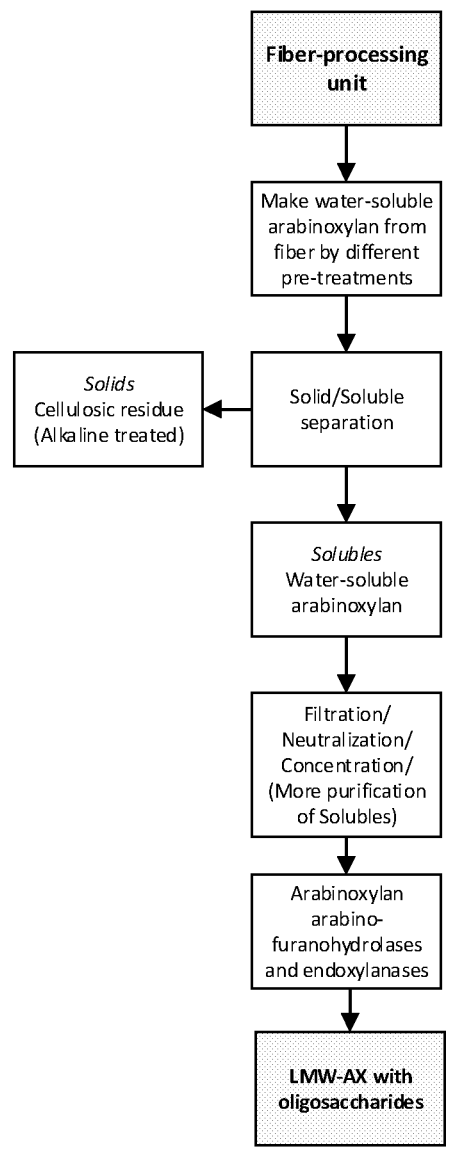

FIG. 9. Flow chart describing the fiber-processing operations in connection to an ethanol process to obtain LMW-AX with oligosaccharides.

Figure 10:
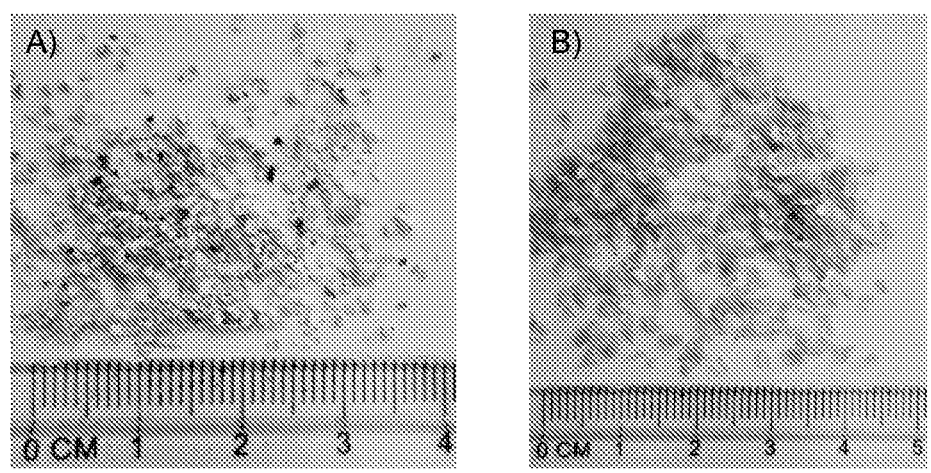

FIG. 10. A) Picture of corn stillage sample and B) picture of fractionated fiber from corn stillage sample.

FIG. 11. HPAEC-PAD chromatogram showing oligosaccharides present in samples of enzymatically hydrolyzed corn arabinoxylan. Different combinations of endoxylanase and arabinoxylan arabinofuranohydrolases have been used. "+" sign indicate that the enzymes are used at the same time in an enzyme cocktail while the "→" sign indicate that the enzyme treatments have been sequential with an enzyme inactivation step between.

Figure 12:
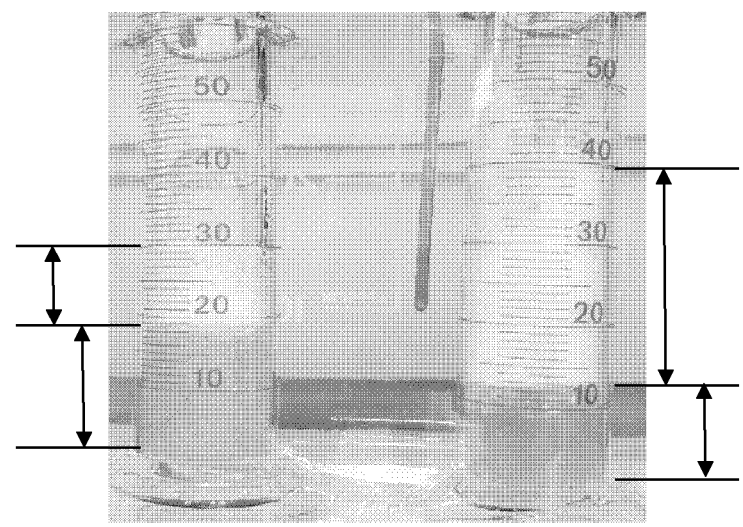

FIG. 12. Picture of foam produced by washed fiber (left) and de-starched corn bran (right) with alkaline hydrogen peroxide treatment.

DETAILED DESCRIPTION OF THE INVENTION

LMW-AX with branched oligosaccharides was prepared from a cereal fiber containing AX by alkaline hydrogen peroxide extraction followed by incubation with an AX specific endoxylanase.

In the first example a fiber is isolated from a sample of corn stillage (FIG. 4A) by fractionation and washing of the fiber (FIG. 4B). The fiber is processed by alkaline hydrogen peroxide to yield water-soluble AX with a high yield 76-88% based on recovered AX or on remaining AX in the solid fraction respectively. The soluble phase is then separated and dialyzed to remove colored components and salts. Finally the water-soluble AX after dialysis is incubated with an AX specific endoxylanase to yield LMW-AX with branched oligosaccharides (FIG. 4C) and a cellulosic solid residue (FIG. 4D). The sugar composition of corn stillage, washed fractionated fiber and LMW-AX with branched oligosaccharides is shown in Table 1. The purity of water-soluble AX can be further improved by an optional protease treatment before the dialysis. The purity of LMW-AX with branched oligosaccharides can be further improved by ultra-filtration and nanofiltration to recover the added xylanase and to remove the added $CaCl_2$ respectively.

A comparison with endoxylanases from family 10 and 11, the most commonly used xylanase families to produce LMW-AX, showed that the AX specific endoxylanase was much more efficient in producing branched oligosaccharides from corn AX (FIG. 5A). These oligosaccharides were confirmed to be branched by incubating the sample with two arabinofuranosidases that selectively removed Araf units attached to the oligosaccharides (FIG. 5B). The LMW-AX with branched oligosaccharides obtained by the AX specific endoxylanase contained no detectable β-(1→4) linked XOS or xylose which means that all the products produced by this type of enzymes are truly branched or (1→3) linked disaccharides as opposed to hydrolysis products obtained with a family 10 or 11 xylanase (FIG. 5A).

Isolated water-soluble AX from corn fiber had an average molecular weight of 55 kDa and cotton white in color after dialysis. After incubation with the AX specific endoxylanase the average molecular weight decreased to 2.5 kDa corresponding to 18-19 sugar units. This experiment proved that an AX specific endoxylanse is excellent in producing branched oligosaccharides even from complex AX substrates such as isolated from corn. While state of the art processes that use either family 10 or 11 xylanases are less efficient in hydrolyzing complex AX and cannot produce sufficient amounts of oligosaccharides (FIG. 5A). Analysis of the Mw obtained by the family 10 xylanase revealed that this xylanase family can only reduce the molecular weight to 24 kDa while family 11 did not reduce the molecular weight at all (55 kDa). This explains why very few oligosaccharides are obtained using the family 10 xylanase and why family 11 xylanases are unable to hydrolyse corn AX (FIG. 5A). This motivates using a chemical pre-treatment such as alkaline extraction in combination with an AX specific endoxylanase to obtain LMW-AX with branched oligosaccharides.

The cellulosic residue obtained after corn fiber alkali hydrogen peroxide extraction had a cellulose content of 36% and an AX content of 14% (A/X=0.38) based on dry mass. This residue can be added back to a process stream introducing an easily digestible cellulosic fiber for ruminant animals. Alternatively this residue could be used as a cellulosic ethanol feedstock or as a food additive.

Detailed Description of LMW-AX with Branched Oligosaccharides from Corn Fiber

Average molecular weight: 2.5 kDa

A/X ratio: 0.56

Contain branched oligosaccharides with at least one (1→3) linked Araf or (1→3) linked Xylp unit on the reducing end xylose of the backbone. Can also contain two different disaccharides consisting of (1→3) linked xylose-xylose (D-xylopyranose-β-(1→3)-xylose) or arabinose-xylose (L-arabinofuranose-α-(1→3)-xylose).

TABLE 1

Total sugar composition (g/g), arabinoxylan content (% dry mass) and arabinose to xylose ratio (A/X) of corn stillage, isolated corn fiber, water-soluble AX from corn fiber and LMW-AX with branched oligosaccharides from corn AX. Table 1 also shows the total sugar composition (g/g), arabinoxylan content (% dry mass) and arabinose to xylose ratio (A/X) of front separated fiber (corn bran) and de-starched front separated fiber (corn bran).

| Sample | Arabinose | Galactose | Glucose | Xylose | Arabinoxylan content (% dry mass) | A/X |
|---|---|---|---|---|---|---|
| Corn stillage | 0.06 | 0.02 | 0.15 | 0.09 | 13 | 0.58 |
| Isolated corn fiber | 0.15 | 0.04 | 0.14 | 0.31 | 40 | 0.48 |
| Water-soluble AX from corn fiber | 0.24 | 0.06 | 0.01 | 0.43 | 59 | 0.55 |
| LMW-AX with branched oligosaccharides from corn AX | 0.22 | 0.06 | 0.01 | 0.40 | 54 | 0.56 |
| Front separated fiber (corn bran) | 0.09 | 0.03 | 0.35 | 0.19 | 25 | 0.47 |
| De-starched front separated fiber (corn bran) | 0.13 | 0.04 | 0.09 | 0.29 | 37 | 0.45 |

Note:
AX content is calculated as (arabinose + xylose) × 0.88. The relatively lower arabinoxylan content in LMW-AX with branched oligosaccharides from corn AX relative to Water-soluble AX from corn fiber is due to the added $CaCl_2$ and enzyme to the reaction mix.
A/X: arabinose to xylose ratio.

In the second example a highly branched AX fraction (A/X=0.88 and average molecular weight of 87 kDa) is isolated by alkaline hydrogen peroxide from wheat bran (A/X=0.55 and 26% AX on dry mass basis) and treated with an AX specific endoxylanase. A low branched AX fraction A/X=0.34 was removed by lowering the pH of the extract prior to enzyme treatment. Alternatively not lowering the pH and keeping both AX fractions in the same fraction would result in a substrate with an average A/X of 0.81.

LMW-AX with branched oligosaccharides was obtained by hydrolysis of the highly branched AX fraction (A/X of 0.88) with an arabinoxylan specific endoxylanase. The resulting LMW-AX was fractionated using SEC and the fractions were freeze dried, weighted and analyzed for their arabinose to xylose ratios (Table 2).

TABLE 2

Fractions 1-5, percent of mass, molecular weight range and A/X ratio of LMW-AX with branched oligosaccharides produced from highly branched wheat bran arabinoxylan.

| Fraction | Percent of total mass | Mw range (kDa) | A/X |
| --- | --- | --- | --- |
| I | 12.2% | 88.3-24.5 | 0.94 |
| II | 6.4% | 24.5-6.8 | 0.99 |
| III | 32.6% | 6.8-1.9 | 0.85 |
| IV | 43.6% | 1.9-0.53 | 0.85 |
| V | 5.2% | 0.53-0.15 | 0.85 |

An AX specific endoxylanase is highly efficient in hydrolyzing very complex AX from wheat bran. The majority of the hydrolysis products (76.2%) are in the range 6.8-0.5 kDa in size corresponding to 52-5 sugar units and 43.6% are in the range 1.9-0.5 kDa in size corresponding 14-5 sugar units which means that there is a large portion of branched oligosaccharides present in the LMW-AX sample. This is also confirmed by the results obtained from HPAEC-PAD oligosaccharide analysis (FIG. 6), where fraction III and IV contains most of the branched oligosaccharides.

Detailed Description of LMW-AX with Branched Oligosaccharides from Wheat Bran

Average molecular weight: 3.6 kDa

A/X ratio: 0.88 and 0.85 for the fraction that is less than 5 kDa in size.

Contain branched oligosaccharides with at least one (1→3) linked Araf or (1→3) linked Xylp unit on the reducing end xylose of the backbone. Can also contain two different disaccharides consisting of (1→3) linked xylose-xylose (D-xylopyranose-β-(1→3)-xylose) or arabinose-xylose (L-arabinofuranose-α-(1→3)-xylose).

One aspect of the present invention relates to a process for production of water-soluble arabinoxylan or arabinoxylan derived oligosaccharides by isolation of fiber from a cereal ethanol plant. One embodiment relates to a process wherein the fibers are isolated from at least one of the group consisting of the kernel, wet process streams or dry DDGS. Another embodiment relates to a process wherein the cereal ethanol plant is a dry mill ethanol plant. Another embodiment relates to a process wherein the water-soluble arabinoxylan or arabinoxylan derived oligosaccharides are obtained using treatment of wet fractionated fiber with alkali, acid, steam or enzymes. The wet fractionated fiber may be from dry mill ethanol plants, but not exclusively. Another embodiment relates to a process wherein an obtained fraction of the arabinoxylan or arabinoxylan derived oligosaccharides is introduced into a stream for production a prebiotic product. Also other additives are thinkable to add into the stream for the purpose to enhance the end product. Another embodiment relates to a process wherein an obtained fraction of the arabinoxylan or arabinoxylan derived oligosaccharides is introduced into a stream for production of feed to obtain a prebiotic feed product. Another embodiment relates to a process wherein an obtained fraction of the arabinoxylan or arabinoxylan derived oligosaccharides is introduced into a stream of said cereal ethanol plant. Another embodiment relates to a process wherein spent solids remaining after production of water-soluble arabinoxylan or arabinoxylan derived oligosaccharides are introduced into a stream for production of feed products. The spent solids may be introduced as a modified fiber that aid in digestion in ruminant animals. Further, the present invention may comprise a fiber processing unit comprising a reaction unit adapted for an extraction or hydrolysis, and neutralization; a separation unit adapted for at least one solid/liquid separation.

Another aspect of the present invention relates to a product comprising water-soluble arabinoxylan or arabinoxylan derived oligosaccharides obtainable by the process according to the present invention. Another aspect of the present invention relates to the use of the process according to the present invention, for the production of water-soluble arabinoxylan or arabinoxylan derived oligosaccharides. Yet another aspect of the present invention relates to a food, feed, beverage ingredient, or nutritional supplement comprising the water-soluble arabinoxylan or arabinoxylan derived oligosaccharides obtainable by the process according to the present invention.

In another example alkaline hydrogen peroxide extraction was repeated once to increase the concentration of water-soluble AX in the extraction liquid. The results showed that repeating the extraction a second time did not significantly reduce the yield of extracted AX, 79% and 78% for extraction 1 and 2 respectively. Instead repeating the extraction by re-using the extraction liquid increased the concentration of water-soluble AX by 98%, from 15.5 g/L to 30.7 g/L in the first extraction to the second respectively. In one embodiment the concentration of water-soluble AX is 15 g/L to 35 g/L. This exemplifies that re-using the extraction liquid for one time or multiple times is useful to increase the water-soluble AX content, thereby reducing the need for chemicals and making down-stream processing more efficient. The quality of the cellulosic solids were similar for each extraction, demonstrating that re-using the extraction liquid does not change the characteristics of the cellulosic solids significantly.

In another example water-soluble AX from alkaline hydrogen peroxide extraction was purified by calcium chloride precipitation. The calcium chloride was added after the solution was neutralized to pH 7.5 by carbon dioxide. Upon adding the calcium chloride solution a white precipitate formed instantly. The precipitate consisted of calcium carbonate which co-precipitates contaminants from the solution increasing the purity of the water-soluble AX by 31%, from 59% to 77% by selectively removing non-sugar molecules from the solution. In one embodiment the increase in concentration of water-soluble AX is from 59% to 77%. The loss of AX was not significant showing the potential of purifying water-soluble arabinoxylan in a cost efficient way. The only requirement necessary is to de-salt the water-soluble arabinoxylan by for example ultra-filtration to reach a purity exceeding 70% on dry mass basis.

TABLE 3

Total arabinoxylan content (% dry mass) after
dialysis of water-soluble arabinoxylan samples

| Sample | Arabinoxylan content (% dry mass) |
|---|---|
| Water-soluble AX from corn fiber | 59 |
| Calcium salt treated water-soluble AX from corn fiber | 77 |

In another example two different fiber sources where compared with regard to foaming during alkaline hydrogen peroxide extraction. The results as shown in FIG. 12 exemplify the importance to use a fiber source that is washed to remove contaminants. Having a fiber source with more than 40% AX on dry matter basis and reduced amount of protein significantly reduced foam during alkaline extraction. By using a washed fiber source with 41% AX on dry mass basis compared to de-starch front separated fiber (corn bran) reduced the foam fivefold from 50 ml down to 10 ml using a total extraction volume of 20 ml. This means that choosing a fiber with more than 40% AX seems crucial to reduce foaming problems during extraction. This example shows that it is crucial to use a fiber with a high AX content to reduce problems with foaming during alkaline hydrogen peroxide extraction.

LMW-AX with oligosaccharides was prepared from a cereal fiber containing AX by alkaline hydrogen peroxide extraction followed by incubation with arabinofuranosidases and an endoxylanase.

A fraction of the easily removable Araf units was removed in order to open up holes in the AX structure for xylanase hydrolysis, thereby facilitating the production of oligosaccharides from a complex AX substrate.

In the first example a fiber is isolated from a sample of corn stillage (FIG. 4A) by fractionation and washing of the fiber (FIG. 4B). The fiber is processed by alkaline hydrogen peroxide to yield water-soluble AX with a high yield 76-88% based on recovered AX or on remaining AX in the solid fraction respectively. The soluble phase is then separated and dialyzed to remove colored components and salts. Finally the water-soluble AX after dialysis is incubated with a combination of different arabinoxylan arabinofuranohydrolases (AXHs) and a representative endoxylanase from family 10. The resulting oligosaccharides were analyzed on HPAEC-PAD to evaluate which combination of enzymes yields the highest amount of oligosaccharides (FIG. 11). The sugar composition of corn stillage washed fractionated fiber and LMW-AX with oligosaccharides is shown in Table 1. The purity of water-soluble AX can be further improved by an optional protease treatment before the dialysis. The purity of LMW-AX with oligosaccharides can be further improved by ultrafiltration and nanofiltration to recover the added enzymes and to remove the monosaccharides respectively.

A comparison using only an endoxylanase, the most commonly used xylanase activity to produce oligosaccharides, showed that the endoxylanase alone was not efficient in hydrolyzing the AX substrate into oligosaccharides. Instead the additions of arabinofuranosidases, that selectively removed Araf units, were necessary to have a more efficient production of oligosaccharides from corn AX (FIG. 11).

Isolated water-soluble AX from corn fiber had an average molecular weight of 55 kDa and cotton white in color after dialysis. Analysis of the Mw obtained after incubation with a xylanase 10 revealed that this xylanase alone can only reduce the molecular weight to more than 24 kDa. This demonstrates that additional enzymes are necessary for generating oligosaccharides. Only after incubation with an enzyme cocktail comprising both arabinofuranosidases and xylanases there was a reduction in the Mw. Two fractions were obtained, one with a higher Mw of 10-20 kDa and a low Mw of 0.4-10 kDa. This motivates using arabinofuranosidases together with xylanases to obtain LMW-AX with oligosaccharides from complex or densely substituted AX. The experiment also showed that there are more oligosaccharides formed by simultaneous enzymatic treatment with arabinofuranosidases and xylanases than if the treatment is performed in a sequence. Therefore, an enzyme cocktail comprising arabinofuranosidases and xylanases is the preferred method for generating oligosaccharides.

The cellulosic residue obtained after corn fiber alkali hydrogen peroxide extraction had a cellulose content of 36% and an AX content of 14% (A/X=0.38) based on dry mass. This residue can be added back to a process stream introducing an easily digestible cellulosic fiber for ruminant animals. Alternatively this residue could be used as a cellulosic ethanol feedstock or as a food additive.

Detailed Description of LMW-AX with Oligosaccharides from Corn Fiber
Molecular weight: 0.4-20 kDa
A/X ratio: 0.4-0.5

TABLE 4

Total sugar composition (g/g), arabinoxylan content (% dry mass) and arabinose to xylose ratio (A/X) of corn stillage, isolated corn fiber, water-soluble AX from corn fiber and LMW-AX with oligosaccharides from corn AX

| Sample | Arabinose | Galactose | Glucose | Xylose | Arabinoxylan content (% dry mass) | A/X |
|---|---|---|---|---|---|---|
| Corn stillage | 0.06 | 0.02 | 0.15 | 0.09 | 13 | 0.58 |
| Isolated corn fiber | 0.15 | 0.04 | 0.14 | 0.31 | 40 | 0.48 |
| Water-soluble AX from corn fiber | 0.24 | 0.06 | 0.01 | 0.43 | 59 | 0.55 |
| LMW-AX with oligosaccharides from corn AX | 0.17 | 0.08 | 0.02 | 0.38 | 48 | 0.44 |

TABLE 4-continued

Total sugar composition (g/g), arabinoxylan content (% dry mass) and arabinose to xylose ratio (A/X) of corn stillage, isolated corn fiber, water-soluble AX from corn fiber and LMW-AX with oligosaccharides from corn AX

| Sample | Arabinose | Galactose | Glucose | Xylose | Arabinoxylan content (% dry mass) | A/X |
|---|---|---|---|---|---|---|
| obtained using a cocktail of GH10 + AXH-m2,3 + AXH-d3 | | | | | | |

Note:
AX content is calculated as (arabinose + xylose) × 0.88. The relatively lower arabinoxylan content in LMW-AX with oligosaccharides from corn AX relative to Water-soluble AX from corn fiber is due to the enzyme added to the reaction mix.
A/X: arabinose to xylose ratio.

In one embodiment the present invention relates to a composition comprising Low Molecular Weight-Arabinoxylan (LMW-AX) with oligosaccharides, where a fraction of the Araf units have been removed to improve the yield of oligosaccharides. In another embodiment the Low Molecular Weight-Arabinoxylan (LMW-AX) with oligosaccharides comprise Arabinose and Xylose units, preferably with an Arabinose/Xylose ratio of 0.4-1.0, preferably a ratio of 0.4-0.9, preferably a ratio of 0.4-0.8, preferably a ratio of 0.4-0.7, preferably a ratio of 0.4-0.6, preferably a ratio of 0.4-0.5. In another embodiment the average molecular weight is less than 10 kDa, preferably less than 7.5 kDa, preferably less than 5 kDa, preferably less than 2.5 kDa, preferably less than 2 kDa. In another embodiment of the present invention a yield of oligosaccharides is improved by combining a xylanase with arabinofuranosidases, preferentially ones able to remove α-(1→3)-linked Arafat double substituted Xylp units (dXyl) or able to remove single α-(1→2)-linked and α-(1→3)-linked Arafat single substituted Xylp units (mXyl). Preferably using a combination of the two different activities of arabinofuranosidases to obtain a high yield of oligosaccharides; In another embodiment the arabinofuranosidases are selected from the group Arabinoxylan arabinofuranohydrolases (AXHs), preferably selected from the group consisting of arabinoxylan arabinofuranohydrolase-d3 (AXH-d3) or arabinoxylan arabinofuranohydrolase-m2,3 (AXH-m2,3). In another embodiment, the arabinofuranosidase treatment is replaced by a treatment with a weak acid solution before the xylanase treatment, such as, but not limited to, inorganic acids, preferably hydrochloric acid, preferably sulfuric acid, preferably phosphoric acid, preferably nitric acid or preferably acetic acid. In another embodiment the arabinofuranosidase treatment is replaced by a treatment with steam or hot pressurized water before the xylanase treatment, such as, steam explosion or autohydrolysis. In another embodiment the xylanase is an endoxylanase, preferably from family 8, 10 or 11, more preferably from family 10 or 11, most preferably from family 10. In another embodiment the present invention is a composition wherein the substrate is a fiber isolated from at least one of a fiber containing kernel, fiber containing wet process streams or dry Dried Distillers Grains with Solubles (DDGS), preferably from cereals comprising fibers, preferably cereals comprising arabinoxylan.

Another aspect of the present invention relates to a process wherein the starting material is a fiber isolated from at least one of a fiber containing kernel, fiber containing wet process streams or dry Dried Distillers Grains with Solubles (DDGS), preferably from cereals comprising fibers, preferably cereals comprising arabinoxylan, preferably a highly or densely substituted arabinoxylan fraction. In another embodiment the starting material is obtained from a cereal ethanol plant, preferably a dry mill ethanol plant. In another embodiment the arabinoxylan is a water-soluble arabinoxylan, preferably obtained using a pre-treatment of the fiber with alkali, acid, autohydrolysis, steam explosion, milling, cavitation or enzymes. In another embodiment low substituted AX is precipitated by acidification of an alkali extraction solution, and preferably is removed. In another embodiment the water-soluble arabinoxylan is obtained using a pre-treatment comprising at least one of HCl, $H_2SO_4$, NaOH, $Ca(OH)_2$, $NH_4$, or alkaline hydrogen peroxide. In another embodiment, any cellulosic solids remaining after the pre-treatment is reintroduced into a stream from a cereal ethanol plant, preferably a dry mill ethanol plant. In another embodiment the process is for production of feed products. In another embodiment the present invention comprises a fiber processing unit including a reaction unit adapted for alkali extraction and neutralization, or autohydrolysis, or acid hydrolysis and neutralization, or cavitation, or steam explosion, or milling; and a separation unit adapted for at least one solid/liquid separation.

Another aspect of the present invention relates to use of a composition according to the present invention or an obtained fraction of LMW-AX with oligosaccharides from the process according to the present invention, preferably for introduction into a stream of a cereal ethanol plant, preferably a dry mill ethanol plant. Another embodiment relates to use of the present invention for production of a prebiotic product, preferably food, feed, beverage ingredient or nutritional supplements.

Another aspect of the present invention relates to a food, feed, beverage ingredient, or nutritional supplement or a personal care product ingredient, comprising the LMW-AX with oligosaccharides according to the present invention or obtainable by the process according to the present invention.

EXAMPLES

Example 1: Preparation of LMW-AX with Branched Oligosaccharides from Fractionated Corn Fiber Materials and Methods
Enzymes Arabinoxylan specific endoxylanase (Arabinoxylanase) from *Clostridium thermocellum* (CtXyl5A) was purchased from Nzytech (Lisboa, Portugal). A family 10 xylanase from

*Rhodothermus marinus* (RmXyn10A) was prepared as described in Falck et al. (2013). Pentopan mono bg, a commercial family 11 xylanase was obtained from Novozymes (Bagsvaerd, Denmark). High purity recombinant α-L-arabinofuranosidases (E-ABFCJ and E-AFAM2) were purchased from Megazyme (Wicklow Ireland).

Substrate

A sample of dry corn stillage was received from an U.S. corn dry mill ethanol producer. A sample of 27 g was sieved through 1 mm and the large fiber particles separated out by hand and washed with water and then freeze dried.

Process Steps

Freeze-dried fiber (150 mg) was extracted with a 2% (w/w) $H_2O_2$ solution (Sigma) adjusted to pH 11.5 by 50% NaOH (Merck). Equal volumes of freshly prepared alkaline $H_2O_2$ solution was added at time intervals 0, 20 and 40 min to a final dry weight content of 5%. Antifoam TRITON X-100 was added to reduce foaming. The extraction temperature was 90° C. and the total extraction time was 90 min. The reaction was performed in a glass tube with continuously stirring using a magnetic bar.

After the extraction the soluble and insoluble phases where separated by centrifugation at 3900 g for 10 min. The pellet was washed once with 5 volumes of deionized water and centrifuged again to recover remaining solubles trapped in the pellet. Carbon dioxide in the form of dry ice was added to neutralize the soluble and insoluble phase. The soluble fraction was dialyzed against deionized water in a 3.5 kDa dialysis bag (Spectra/por, Spectrum labs, USA) for 24 h. After dialysis the sample was recovered as water-soluble corn arabinoxylan and a fraction was taken out and freeze dried. The solid cellulosic fraction was freeze-dried and a mass corresponding to 34% of the initial fiber was recovered.

Xylanase incubations were all performed using 1.25% of enzyme on arabinoxylan dry basis at pH 7 and 50° C. for 24 h. The reactions were incubated in a water bath. LMW-AX with branched oligosaccharides described in the present invention was produced from 40 mg of dry weight water-soluble corn arabinoxylan by the arabinoxylan specific endoxylanase CtXyl5A with 2 mM $CaCl_2$ added to the reaction mix. After the reaction all samples were freeze-dried.

Characterization of branched oligosaccharides in the sample was performed by incubating the sample with 1.0 U/mg of two different arabinofuranosidases removing (1→3) double linked arabinofuranosyl units (E-AFAM2) or single linked (1→2) or (1→3) arabinofuranosyl units (E-ABFCJ) respectively. The reaction was performed at pH 5.8 using a 20 mM sodium phosphate buffer at 50° C. for 24 h.

Characterization of Total Sugars

Total sugar composition of the water-soluble arabinoxylan and LMW-AX with branched oligosaccharides fractions were hydrolyzed with 2 M TFA for 60 min at 110° C. Neutralization of TFA was done by evaporation. Total sugar composition in corn stillage, isolated corn fiber and the cellulosic residue after alkaline extraction were pre-hydrolyzed with 72% $H_2SO_4$ for 1 h at 30° C. after which the samples were diluted to 4% H2SO4 and hydrolyzed at 100° C. for 3 h. Neutralization of H2SO4 was done by adding Ca(OH)2. Analysis of the recovered neutral monosaccharides from TFA and H2SO4 hydrolysis were done by HPAEC-PAD using a CarboPac PA20 column (250 mm×3 mm, 5.5 µm) and a mobile phase of 20 mM NaOH at 0.5 mL/min. Monosaccharide standards (SIGMA) were as follows: arabinose, galactose, glucose and xylose. Total arabinoxylan content in the samples was calculated as 0.88 times (% arabinose+% xylose) after subtracting any free arabinose. Total cellulose content in the cellulose sample was calculated as 0.90 times % glucose after subtracting any free glucose.

Characterization of Oligosaccharides

Analysis of the obtained oligosaccharides was done by High-Performance Anion-Exchange Chromatography Coupled with Pulsed Electrochemical Detection (HPAEC-PAD) using (ICS-5000) using a CarboPac PA200 column (250 mm×3 mm, 5.5 µm) and a mobile phase of 100 mM NaOH at 0.5 mL/min and a linear gradient (0-30 min) of 0-120 mM of sodium acetate (Sigma). Monosaccharide, xylo-oligosaccharide and arabinoxylo-oligosaccharide standards used were as follows: arabinose and xylose (Sigma), xylobiose, xylotriose, xylotetraose, xylopentaose, xylohexaose, arabinoxylobiose and arabinoxylotriose (Megazyme). All samples were filtered through a 0.22 µm filter before analysis. Determination of branched oligosaccharides was done by incubating the branched low molecular weight arabinoxylan sample with two different arabinofuranosidases as described above, releasing double and single Araf units, and analyzing the sample on HPAEC-PAD.

Characterization of Molecular Weight

Analysis of molecular weight was determined using by high-performance liquid chromatography (HPLC; Dionex Ultimate 3000) with an IR detector (RI-101, Shodex, Japan) using a column for polysaccharide analysis (Shodex, Japan) SB-806HQ and a mobile phase (0.5 mL min-1) of constant 25 mM sodium acetate buffer pH 5.0. Injection volume was 20 µL. Standards were used containing pullulan standards (Shodex, Japan) with molecular weights P-400 ($36.6 \times 10^4$), P-200 ($20.0 \times 10^4$), P-100 ($11.3 \times 10^4$), P-50 ($4.88 \times 10^4$), P-20 ($2.17 \times 10^4$), P-10 ($1.00 \times 10^4$) and P-5 ($0.62 \times 10^4$) and xylose based standards xylohexaose (MW=810.7 Da) (Megazyme, Ireland) and xylose (MW=150.13 Da) (Sigma).

Example 2: Preparation of LMW-AX with Branched Oligosaccharides from Wheat Bran

Enzymes

Arabinoxylan specific endoxylanase (Arabinoxylanase) from *Clostridium thermocellum* (CtXyl5A) was purchased from Nzytech (Lisboa, Portugal). Thermostable α-amylase 0.12 U/g (Thermamyl) and protease (Neutralse 0.8 L) were purchased from Sigma.

Substrate

Commercial wheat bran (Lantmännen Mill Malmö, Sweden) was used as starting material. A fraction of the bran was grinded in a knife mill (FOSS) through a 1.5 mm mesh size for analysis of total sugars.

Process

A suspension (1:9 w/v) of 250 g wheat bran (94% dry mass) in 2.5 L DI water was adjusted to pH 6.0 with HCl 8 M and treated with a thermostable α-amylase 0.12 U/g for 90 min at 90° C. to hydrolyse the starch. The bran was then rinsed with hot tap water to remove solubles until a clear permeate was obtained. A new suspension in water (1:9 w/v) was prepared to remove proteins by incubating the bran with a protease 0.035 U/g for 4 h at 50° C. Thereafter the bran was rinsed with hot tap water, then with DI water and then vacuum dried.

De-starched and de-proteinized wheat bran (50 g dry weight) was extracted with 1 L of a dilute alkaline solution of sodium hydroxide containing 2% hydrogen peroxide at pH 11.5 for 4 h at 60° C. with 200 rpm stirring. Antifoam TRITON X-100 was added to reduce foaming. After the extraction solids were removed by filtration and the solution was centrifuged (SIGMA) 6000 g for 20 min. The supernatant was neutralized with 8 M HCl and horseradish peroxidase was added to remove remaining hydrogen peroxide. The extract containing AX (A/X=0.81) was centrifuged again at 6000 g for 20 minutes to remove precipitate.

The recovered supernatant was then adjusted to pH 4.0 and left for 3 h to precipitate low branched AX (A/X=0.34). The highly branched fraction of AX (A/X=0.88) was recovered by centrifugation at 6000 g for 20 minutes and the low branched AX discarded. The supernatant after centrifugation was neutralized with NaOH to pH 7. A protease 0.00125 U/mL was added and the sample was incubated at 50° C. overnight. AX was recovered from the solution by ethanol precipitation to a final concentration of 80% and the sample was left stirring for 1 h. The precipitated AX was recovered by centrifugation 3000 g for 3 min. The pellet was washed once with 80% ethanol and recovered by centrifugation. The pellet was then left to air dry and then dissolved in MQ water at 50° C. and the pH adjusted to 7 with NaOH.

Xylanase incubation of 30 mL of highly substituted water-soluble wheat bran arabinoxylan was performed at 50° C. for 24 h using a water bath. Arabinoxylan specific endoxylanase CtXyl5A (0.5 mg) was used to hydrolyze the arabinoxylan. In the reaction mix was also 2 mM $CaCl_2$ in order to stabilize the enzyme. After the reaction the sample was freeze dried and referred to as LMW-AX with branched oligosaccharides from wheat bran.

Characterization of Total Sugars

Total sugar composition of the water-soluble arabinoxylan and LMW-AX with branched oligosaccharides and isolated fractions from SEC were hydrolyzed with 2 M TFA for 60 min at 110° C. Neutralization of TFA was done by evaporation. Total sugar composition in milled wheat bran was determined by pre-hydrolyzed with 72% $H_2SO_4$ for 1 h at 30° C. after which the sample was diluted to 4% H2SO4 and hydrolyzed at 100° C. for 3 h. Neutralization of H2SO4 was done by adding Ca(OH)2. Analysis of the recovered neutral monosaccharides from TFA and H2SO4 hydrolysis were done by HPAEC-PAD using a CarboPac PA20 column (250 mm×3 mm, 5.5 µm) and a mobile phase of 20 mM NaOH at 0.5 m L/min. Monosaccharide standards (SIGMA) were as follows: arabinose, galactose, glucose and xylose. Total arabinoxylan content in the samples was calculated as 0.88 times (% arabinose+% xylose) after subtracting any free arabinose.

Characterization of Oligosaccharides

Analysis of oligosaccharides was done by High-Performance Anion-Exchange Chromatography Coupled with Pulsed Electrochemical Detection (HPAEC-PAD) using (ICS-5000) using a CarboPac PA200 column (250 mm×3 mm, 5.5 µm) and a mobile phase of 100 mM NaOH at 0.5 mL/min and a linear gradient (0-30 min) of 0-120 mM of sodium acetate (Sigma). Monosaccharide, xylo-oligosaccharide and arabinoxylo-oligosaccharide standards used were as follows: arabinose and xylose (Sigma), xylobiose, xylotriose, xylotetraose, xylopentaose, xylohexaose, arabinoxylobiose and arabinoxylotriose (Megazyme).

Characterization of Molecular Weight and Fraction Collection

Analysis of molecular weights and fraction collection was done using a Sephacryl S-200 HR column (600×16 mm) and an IR detector and a mobile phase (0.3 mL min-1) of constant degassed filtered water. A 2.5 mL sample with 10 g/L of LMW-AX with branched oligosaccharides obtained by arabinoxylan hydrolysis with the arabinoxylan specific endoxylanase CtXyl5A was filtered through a 0.45 µm and injected. Fractions of 3 mL were collected. Fractions were pooled together for 5 different time interval (60 min each) and freeze dried. Standards were used to calculate the molecular weight range of each fraction using pullulan standards (Shodex, Japan) with molecular weights P-400 ($36.6 \times 10^4$), P-200 ($20.0 \times 10^4$), P-100 ($11.3 \times 10^4$), P-50 ($4.88 \times 10^4$), P-20 ($2.17 \times 10^4$), P-10 ($1.00 \times 10^4$) and P-5 ($0.62 \times 10^4$). Also xylose based standards xylohexaose (MW=810.7 Da) (Megazyme, Ireland) and xylose (MW=150.13 Da) (Sigma) were used.

Example 3: Preparation of LMW-AX with Oligosaccharides from Fractionated Corn Fiber Materials and Methods
Enzymes A family 10 xylanase from *Rhodothermus marinus* (RmXyn10A) was prepared as described in Falck et al. (2013). High purity recombinant α-L-arabinofuranosidases were purchased from Megazyme (Wicklow Ireland): *Cellvibrio japonicus* (E-ABFCJ) removing Araf from (1→2) or (1→3) single substituted Xylp units, mXyl2 and mXyl3 respectively, referred to as AXH-m2,3 in the text and FIG. 11. *Bifidobacterium adolescentis* (E-AFAM2) removing (1→3) Araf from double (1→2) and (1→3) substituted Xylp units, dXyl, referred to as AXH-d3 in the text and in FIG. 11.
Substrate A sample of dry corn stillage was received from an U.S. corn dry mill ethanol producer. A sample of 27 g was sieved through 1 mm and the large fiber particles separated out by hand and washed with water and then freeze dried.
Process Steps Freeze-dried fiber (150 mg) was extracted with a 2% (w/w) $H_2O_2$ solution (Sigma) adjusted to pH 11.5 by 50% NaOH (Merck). Equal volumes of freshly prepared alkaline $H_2O_2$ solution was added at time intervals 0, 20 and 40 min to a final dry weight content of 5%. Antifoam TRITON X-100 was added to reduce foaming. The extraction temperature was 90° C. and the total extraction time was 90 min. The reaction was performed in a glass tube with continuously stirring using a magnetic bar.

After the extraction the soluble and insoluble phases where separated by centrifugation at 3900 g for 10 min. The pellet was washed once with 5 volumes of deionized water and centrifuged again to recover remaining solubles trapped in the pellet. Carbon dioxide in the form of dry ice was added to neutralize the soluble and insoluble phase. The soluble fraction was dialyzed against deionized water in a 3.5 kDa dialysis bag (Spectra/por, Spectrumlabs, USA) for 24 h. After dialysis the sample was recovered as watersoluble corn arabinoxylan and a fraction was taken out and freeze dried. The solid cellulosic fraction was freeze-dried and a mass corresponding to 34% of the initial fiber was recovered.

LMW-AX with oligosaccharides described in the present invention was produced from water-soluble corn arabinoxylan (10 g/L) by incubating the sample with different combinations of 1.0 U/mg arabinofuranosidases (AXH-m2,3 and/or AXH-d3) and 1% (wt/wt) xylanase (Xyn10). Where the "+" sign indicate that the enzymes are used at the same time in an enzyme cocktail while the "→" sign indicate that the enzyme treatments have been sequential with an enzyme inactivation step by boiling for 15 min have between used between the treatments. All reactions were performed at pH 7 at 50° C. for 24 h. The reactions were incubated in a heat block.

Cocktail Combinations
  Xyn10 only
  Xyn10+AXH-m2,3
  Xyn10+AXH-d3
  Xyn10+AXH-m2,3+AXH-d3
  (AXH-m2,3+AXH-d3)→Xyn10

Characterization of Total Sugars

Total sugar composition of the water-soluble arabinoxylan and LMW-AX with oligosaccharides fractions were hydrolyzed with 2 M TFA for 60 min at 110° C. Neutralization of TFA was done by evaporation. Total sugar composition in corn stillage, isolated corn fiber and the cellulosic residue after alkaline extraction were pre-hydrolyzed with 72% $H_2SO_4$ for 1 h at 30° C. after which the samples were diluted to 4% H2SO4 and hydrolyzed at 100° C. for 3 h. Neutralization of H2SO4 was done by adding Ca(OH)2. Analysis of the recovered neutral monosaccharides from TFA and H2SO4 hydrolysis were done by HPAEC-PAD using a CarboPac PA20 column (250 mm×3 mm, 5.5 µm) and a mobile phase of 20 mM NaOH at 0.5 mL/min. Monosaccharide standards (SIGMA) were as follows: arabinose, galactose, glucose and xylose. Total arabinoxylan content in the samples was calculated as 0.88 times (% arabinose+% xylose) after subtracting any free arabinose. Total cellulose content in the cellulose sample was calculated as 0.90 times % glucose after subtracting any free glucose.

Characterization of Oligosaccharides

Analysis of the obtained oligosaccharides was done by High-Performance Anion-Exchange Chromatography Coupled with Pulsed Electrochemical Detection (HPAEC-PAD) using (ICS-5000) using a CarboPac PA200 column (250 mm×3 mm, 5.5 µm) and a mobile phase of 100 mM NaOH at 0.5 mL/min and a linear gradient (0-30 min) of 0-120 mM of sodium acetate (Sigma). Monosaccharide, xylooligosaccharide and arabinoxylooligosaccharide standards used were as follows: arabinose and xylose (Sigma), xylobiose, xylotriose, xylotetraose, xylopentaose, xylohexaose, arabinoxylobiose and arabinoxylotriose (Megazyme). All samples were filtered through a 0.22 µm filter before analysis on HPAEC-PAD.

Characterization of Molecular Weight

Analysis of molecular weight was determined using by high-performance liquid chromatography (HPLC; Dionex Ultimate 3000) with an IR detector (RI-101, Shodex, Japan) using a column for polysaccharide analysis (Shodex, Japan) SB-806HQ and a mobile phase (0.5 mL min-1) of constant 25 mM sodium acetate buffer pH 5.0. Injection volume was 20 µL. Standards were used containing pullulan standards (Shodex, Japan) with molecular weights P-400 (36.6×10$^4$), P-200 (20.0×10$^4$), P-100 (11.3×10$^4$), P-50 (4.88×10$^4$), P-20 (2.17×10$^4$), P-10 (1.00×10$^4$) and P-5 (0.62×10$^4$) and xylose based standards xylohexaose (MW=810.7 Da) (Megazyme, Ireland) and xylose (MW=150.13 Da) (Sigma).

Example 4 Reuse of Extraction Liquid from Pre-Treatment

In order to increase the concentration of water-soluble arabinoxylan in the extraction liquid without increasing the fiber to extraction liquid ratio, the extraction liquid was re-used in another subsequent extraction.

Substrate

A sample of a separated fiber fraction after fermentation was received from an U.S. corn dry mill ethanol producer. The fiber wash washed with water and filtered through 1 mm filter to recover a fraction with an AX content more than 40% on dry mass basis (41%). The AX content was determined with 72% H2SO4 for 1 h at 30° C. after which the samples were diluted to 4% H2SO4 and hydrolyzed at 100° C. for 3 h. Neutralization of H2SO4 was done by adding Ba(OH)2.

Process for Repeated Extraction

Washed fiber (1.44 g dry weight) was extracted with a 2% (w/w) $H_2O_2$ solution (Sigma) adjusted to pH 11.5 by 50% NaOH (Merck). Equal volumes of freshly prepared alkaline $H_2O_2$ solution was added at time intervals 0, 20 and 40 min to a final dry weight content of 5%. Antifoam TRITON X-100 was added to reduce foaming. The extraction temperature was 90° C. and the total extraction time was 90 min. The reaction was performed in a glass tube with continuously stirring using a magnetic bar.

After the extraction the soluble and insoluble phases where separated by centrifugation at 3900 g for 10 min. The pellet was washed once with 10 ml of deionized water and centrifuged again to recover remaining solubles trapped in the pellet. The wash water was added back with the supernatant to a final volume of 30 ml and sample was taken for sugar analysis. The pH was re-adjusted to 11.5 with NaOH and then the solution was used to extract 1.44 g of washed fiber using the same process as described for the first extraction. After the second extraction the soluble and insoluble phases where separated by centrifugation at 3900 g for 10 min. The pellet was washed once with 10 ml of deionized water and centrifuged again to recover remaining solubles trapped in the pellet. The wash water was added back with the supernatant to a final volume of 30 ml and sample was taken for sugar analysis. Deionized water was added to the two pellets and then carbon dioxide in the form of dry ice was added to neutralize the insoluble phase containing the cellulosic fiber. The pellet was washed another time using 40 ml deionized water to remove remaining salts and then freeze dried.

Characterization of Total Sugars

Total sugar composition of the water-soluble arabinoxylan fractions were hydrolyzed with 2 M TFA for 60 min at 110° C. Neutralization of TFA was done by evaporation. Total sugar composition in washed fiber and the cellulosic residue after alkaline extraction were pre-hydrolyzed with 72% $H_2SO_4$ for 1 h at 30° C. after which the samples were diluted to 4% H2SO4 and hydrolyzed at 100° C. for 3 h. Neutralization of H2SO4 was done by adding Ba(OH)2. Analysis of the recovered neutral monosaccharides from TFA and H2SO4 hydrolysis were done by HPAEC-PAD using a CarboPac PA20 column (250 mm×3 mm, 5.5 µm) and a mobile phase of 20 mM NaOH at 0.5 m L/m in. Monosaccharide standards (SIGMA) were as follows: arabinose, galactose, glucose and xylose. Total arabinoxylan content in the samples was calculated as 0.88 times (% arabinose+% xylose) after subtracting any free arabinose. Total cellulose content in the cellulose sample was calculated as 0.90 times % glucose after subtracting any free glucose.

Example 5: Process for Purification of Water-Soluble Arabinoxylan by Precipitation with Calcium Chloride A supernatant recovered after a second extraction from a process described in example 4 was neutralized to pH 7.5 by adding carbon dioxide in the form of dry ice. A 10 ml sample was dialyzed against deionized water in a 3.5 kDa dialysis bag (Spectra/por, Spectrum labs, USA) for 24 h. After dialysis the sample was recovered as water-soluble corn arabinoxylan and a fraction was taken out and freeze dried. Another 10 ml sample of the supernatant mixed with 3 ml 1 M CaCl2 to precipitate impurities together with CaCO3. The precipitate was removed by centrifugation at 6000 g for 20 min and 10 ml of supernatant was dialyzed as described above and freeze died.

Characterization of Total Sugars

Total sugar composition of the water-soluble arabinoxylan fractions were hydrolyzed with 2 M TFA for 60 min at 110° C. Neutralization of TFA was done by evaporation. Analysis of the recovered neutral monosaccharides from TFA hydrolysis were done by HPAEC-PAD using a CarboPac PA20 column (250 mm×3 mm, 5.5 µm) and a mobile phase of 20 mM NaOH at 0.5 mL/min. Monosaccharide standards (SIGMA) were as follows: arabinose, galactose, glucose and xylose. Total arabinoxylan content in the samples was calculated as 0.88 times (% arabinose+% xylose) after subtracting any free arabinose. Total cellulose content in the cellulose sample was calculated as 0.90 times % glucose after subtracting any free glucose.

Example 6: Comparison of Fiber Sources

In order to compare different fiber sources as substrates for making cellulose, corn fiber gum, and AXOS from two different fiber sources where compared with regard to foam production during extraction. A sample of front separated fiber also known as corn bran was received from a European corn dry mill ethanol producer.

The front separated fiber was de-starched in a suspension (1:9 w/v) of 35.7 g dry mass of corn bran in 0.6 L DI water was adjusted to pH 6.0 with HCl 8 M and treated with a thermostable α-amylase 0.12 U/g for 90 min at 90° C. to hydrolyse the starch. The bran was then rinsed with hot tap water to remove solubles until a clear permeate was obtained. The bran was then freeze dried.

Washed fiber (1.0 g dry weight) and de-starched front separated fiber (corn bran) were extracted with a 2% (w/w) $H_2O_2$ solution (Sigma) adjusted to pH 11.5 by 50% NaOH (Merck). The foam level was recorded once it was stable.

Total sugar composition in front separated fiber (corn bran) and de-starched front separated fiber (corn bran) were pre-hydrolyzed with 72% $H_2SO_4$ for 1 h at 30° C. after which the samples were diluted to 4% H2SO4 and hydrolyzed at 100° C. for 3 h. Neutralization of H2SO4 was done by adding Ba(OH)2. Analysis of the recovered neutral monosaccharides from H2SO4 hydrolysis were done by HPAEC-PAD using a CarboPac PA20 column (250 mm×3 mm, 5.5 µm) and a mobile phase of 20 mM NaOH at 0.5 mL/min. Monosaccharide standards (SIGMA) were as follows: arabinose, galactose, glucose and xylose. Total arabinoxylan content in the samples was calculated as 0.88 times (% arabinose+% xylose) after subtracting any free arabinose. Total cellulose content in the cellulose sample was calculated as 0.90 times % glucose after subtracting any free glucose.

REFERENCES

FALCK, P., PRECHA-ATSAWANAN, S., GREY, C., IMMERZEEL, P., STÅLBRAND, H., ADLERCREUTZ, P., NORDBERG KARLSSON, E. 2013. Xylooligosaccharides from hardwood and cereal xylans produced by a thermostable xylanase as carbon sources for *Lactobacillus brevis* and *Bifidobacterium adolescentis*. *Journal of Agricultural and Food Chemistry* 61, 30, 7333-7340.

The invention claimed is:

1. A process for the production of at least one of water-soluble Arabinoxylan, branched Low Molecular Weight-Arabinoxylan or Low Molecular Weight-Arabinoxylan comprising the steps of:
    A. Isolating starting material comprising a fiber fraction from an ethanol process;
    B. Increasing the concentration of Arabinoxylan in the fiber fraction of step A, by a mechanical process, obtaining a fiber fraction with increased content of Arabinoxylan;
    C. Treating and extracting the fiber fraction with increased Arabinoxylan of step B with an alkaline or alkaline hydrogen peroxide solution, obtaining a solution comprising cellulosic solids and water-soluble Arabinoxylan;
    D. Separating the cellulosic solids of step C from extraction liquid containing water-soluble Arabinoxylan to obtain a step D extraction liquid followed by neutralizing, washing and drying the cellulosic solids;
    E. Optionally repeating extraction of additional fiber fraction re-using the step D extraction liquid, to obtain step E extraction liquid, and optionally repeating step E using the last step E extraction liquid;
    F Reducing the pH, with $CO_2$, of the step D extraction liquid or, if applicable, step E extraction liquid;
    G. Treating the step D extraction liquid or, if applicable, step E extraction liquid with a calcium salt to precipitate impurities and removing precipitate;
    H. Using precipitation or filtration to recover water-soluble Arabinoxylan;
    I. Treating the water-soluble Arabinoxylan with one or more enzymes comprising Arabinoxylan specific endoxylanase to make or Low Molecular Weight-Arabinoxylan or branched Low Molecular Weight-Arabinoxylan; and
    J. Concentrating or drying the Low Molecular Weight-Arabinoxylan products from H and/or I,
    wherein the Arabinoxylan specific endoxylanases specifically hydrolyze substituted regions on an Arabinoxylan molecule to produce (1→3) linked disaccharides and optionally branched poly- or oligo-saccharides as end products,
    wherein the (1→3) linkages of the disaccharides comprise linkages between one arabinose and a xylose unit and optionally between two xylose units.

2. The process according to claim 1, wherein the starting material is a fiber isolated from at least one of a fiber containing kernel, fiber containing wet process streams or dry Dried Distillers Grains with Solubles (DDGS).

3. The process according to claim 1, wherein the starting material is obtained from a cereal ethanol plant.

4. The process according to claim 1, wherein a portion of arabinoxylan having lower substitution is precipitated by acidification of an alkali extraction.

5. The process according to claim 1, wherein the water-soluble Arabinoxylan is obtained using a pre-treatment comprising at least one of HCl, $H_2SO_4$, NaOH, $Ca(OH)_2$, $NH_4$, and alkaline hydrogen peroxide.

6. The process according to claim 5, wherein any cellulosic solids remaining after step D or step E of the process is reintroduced into the starting material.

7. The process according to claim 6, wherein the process is for production of feed products.

8. The process according to claim 1, comprising a fiber processing unit including a reaction unit adapted for alkali extraction and neutralization, or autohydrolysis, or acid hydrolysis and neutralization, or cavitation, or steam explosion, or milling; and a separation unit adapted for at least one solid/liquid separation.

9. The process according to claim 6, wherein the pre-treatment is repeated at least two times.

10. The process according to claim 1, wherein step D extraction liquid or, if applicable, step E extraction liquid containing water-soluble Arabinoxylan is purified by precipitation.

11. The process according to claim 2, wherein the starting material comprises cereal comprising substituted Arabinoxylan.

12. The process according to claim 1, wherein the Arabinoxylan substrate for the Arabinoxylan specific endoxylanase is a water-soluble Arabinoxylan obtained using a pre-treatment of the fiber with alkali, alkaline hydrogen peroxide, acid, autohydrolysis, steam explosion, milling, cavitation or enzymes.

13. The process according to claim 12, wherein the pre-treatment is repeated three or more times.

14. The process according to claim 10, wherein step D extraction liquid or, if applicable, step E extraction liquid containing water-soluble Arabinoxylan is purified by precipitation with calcium salts.

15. The process according to claim 14, wherein the calcium salts comprise calcium hydroxide and/or calcium chloride.

16. The process according to claim 14, wherein the purity of water-soluble Arabinoxylan after calcium salt precipitation and filtration or precipitation is at least 50%.

17. The process according to claim 14, wherein the purity of water-soluble Arabinoxylan after calcium salt precipitation and filtration or precipitation is at least 80%.

18. The process according to claim 14, wherein the purity of water-soluble Arabinoxylan after calcium salt precipitation and filtration or precipitation is at least 90%.

19. The process according to claim 14, wherein the purity of water-soluble Arabinoxylan after calcium salt precipitation and filtration or precipitation is at least 95%.

20. The process according to claim 14, wherein the purity of water-soluble Arabinoxylan after calcium salt precipitation and filtration or precipitation is at least 99%.

* * * * *